United States Patent
Maghrabi et al.

(10) Patent No.: US 11,142,677 B2
(45) Date of Patent: *Oct. 12, 2021

(54) HIGH SOLIDS TOLERANT INVERT EMULSION FLUIDS

(71) Applicant: Ingevity South Carolina, LLC, North Charleston, SC (US)

(72) Inventors: Shadaab S. Maghrabi, Greer, SC (US); Joseph J. Fandel, Charleston, SC (US)

(73) Assignee: INGEVITY SOUTH CAROLINA, LLC, North Charleston, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/866,197

(22) Filed: May 4, 2020

(65) Prior Publication Data

US 2020/0263072 A1   Aug. 20, 2020

Related U.S. Application Data

(63) Continuation of application No. 16/261,925, filed on Jan. 30, 2019, now Pat. No. 10,676,659.
(Continued)

(51) Int. Cl.
  *C09K 8/36* (2006.01)
  *E21B 21/00* (2006.01)
  (Continued)

(52) U.S. Cl.
  CPC .............. *C09K 8/36* (2013.01); *C07C 231/02* (2013.01); *C09K 8/035* (2013.01); *E21B 21/00* (2013.01)

(58) Field of Classification Search
  CPC . C09K 8/36; C09K 8/035; C09K 8/12; C09K 8/03; C09K 8/68; C09K 8/032;
  (Continued)

(56) References Cited

U.S. PATENT DOCUMENTS 8,927,468 B2   1/2015   Hurd et al.

FOREIGN PATENT DOCUMENTS

WO   WO 1989/011516   11/1989
WO   WO 2003/038008   5/2003
(Continued)

OTHER PUBLICATIONS

API STD 65—Part 2, Isolating Potential Flow Zones During Well Construction, Upstream Segment, Second Edition, Dec. 2010. Global Standards.
(Continued)

*Primary Examiner* — Zakiya W Bates
(74) *Attorney, Agent, or Firm* — Bryan D. Zerhusen, Esq.; Nicholas R. Herrel, Esq.; Cantor Colburn LLP

(57) ABSTRACT

A low gravity solid tolerant emulsifier and methods of making the same. The emulsifier includes a maleated amido-amine reaction product produced by: (1) reacting a fatty acid material comprising, and an amine material (e.g., a amine having a amine value of about 700 to about 1300 mg/g, such as AMINE HST) to produce an amido-amine reaction product; and (2) reacting the amido-amine reaction product with maleic anhydride to produce the maleated amido-amine reaction product. An invert emulsion fluids and drilling fluids that include the emulsifier of described herein and methods of using the same.

21 Claims, 2 Drawing Sheets

Related U.S. Application Data

(60) Provisional application No. 62/623,689, filed on Jan. 30, 2018.

(51) Int. Cl.
*C07C 231/02* (2006.01)
*C09K 8/035* (2006.01)

(58) Field of Classification Search
CPC . C09K 8/72; E21B 21/00; E21B 33/13; E21B 37/00; E21B 37/06; E21B 41/02; E21B 43/267
See application file for complete search history.

(56) References Cited

FOREIGN PATENT DOCUMENTS

| WO | WO 2014/070340 | 5/2014 |
|---|---|---|
| WO | WO 2016/086212 | 6/2016 |

OTHER PUBLICATIONS

International Search Report and Written Opinion dated Mar. 25, 2019, for PCT/US2019/015798.

HIGH SOLIDS TOLERANT INVERT EMULSION FLUIDS

CROSS-REFERENCE TO RELATED APPLICATION

The present disclosure is a continuation of U.S. Non-Provisional application Ser. No. 16/261,925, filed 30 Jan. 2019, titled HIGH SOLIDS TOLERANT INVERT EMULSION FLUIDS, which claims priority to U.S. Provisional Application Ser. No. 62/623,689, filed 30 Jan. 2018, the contents of each are incorporated herein by reference in their entirety for all purposes.

FIELD

The present disclosure relates to an invert emulsion fluid composition and associated methods. In particular, the disclosure provides reaction products of amine, low titer fatty acid material, and maleic anhydride as emulsifiers for invert emulsion drilling fluids, and drilling fluid compositions comprising the same. The invert emulsion fluids (IEF) is stable and has high tolerance for low gravity solids (LGS) providing controlled (low) rheology. The present disclosure also provides methods of synthesizing an economic and effective drilling fluid composition for oil and gas drilling.

BACKGROUND

A drilling fluid is a specially designed fluid that is circulated through an oil or gas wellbore as the wellbore is drilled to facilitate the drilling operation. A need exists for an improved additive for modifying and controlling the suspension properties of drilling fluids that would be efficient, easily handled, and readily dispersible in a broad range of drilling muds, and usable under a broad range of conditions.

Drilling fluids or muds are typically classified according to their base fluid or continuous phase, as water base and oil base fluids. Drilling fluids may contain a mixture of base fluids, and are typically classified by the predominating or continuous base fluid, with the fluid present in lesser quantities becoming the internal or emulsified phase. The use of oil and invert oil-based drilling fluids or muds in oil exploration is increasing rapidly owing to the more demanding requirements encountered in drilling deep and/or non-vertical and deviated wells. Compared with the longer-established water-based drilling muds, oil and invert oil-based drilling fluids possess a number of advantages, including reduced interaction with earth formations, and improved lubricity. The drilling fluids and methods of the present disclosure are particularly useful in invert emulsion systems.

Oil based invert emulsion drilling fluids are generally used throughout the world and consist of a three-phase system: oil, internal hygroscopic phase and fine particulate solids. The internal hygroscopic phase can be an aqueous phase typically a brine or it can be an organic compound like glycerol or polyglycerol either dissolved in water or neat or a combination thereof. The addition of brine reduces the overall price of the fluid, reduces the risk of combustion of the oil, builds an emulsion structure that provides suspension and improved viscosity to the fluid, provides improved shale stability by driving water out of the shale and into the fluid via osmosis, and improves the water acceptance of the mud. The brine of choice is commonly an aqueous solution of an inorganic salt, such as sodium chloride or calcium chloride.

Drilling fluids or drilling muds are pumped under pressure down through a long string of drill pipe, then through the center of the drilling bit at the hole bottom, then back up through the annulus between the outside of the string of drill pipe and up the borehole wall to the surface.

Drilling fluids provide a number of interrelated functions to satisfy the requirements of the oil industry for a commercial drilling fluid, which may be grouped as follows. (1) The drilling fluid must suspend and transport solid particles, e.g. drill cuttings, to the surface for screening out and disposal. (2) The drilling fluid must build a filter cake that can prevent the loss of downhole pressure and fluid loss to the formation, including when traversing an interval of porous formation material. (3) The drilling fluid must keep suspended an additive weighting agent (to increase specific gravity of the mud), so that uniform mud weight is maintain throughout the column of drilling fluid in the well, especially when encountering pressurized pockets of combustible gas, which otherwise would tend to reduce downhole pressure, as well as creating a "blowout" in which the fluid and even the drill stem are violently ejected from the well, with resulting catastrophic damages, such as fires. (4) The drilling fluid must constantly lubricate the drill bit so as to promote drilling efficiency and retard bit wear. (5) The drilling fluid should maintain sufficient hydrostatic pressure to manage the wellbore pressure for improved wellbore stability.

It should be noted that a drilling fluid must perform its various functions not only when the drill bit is actively encountering the bottom of the borehole, but also at times when the drill stem is inactive, or is being removed or re-inserted for some purpose. In particular, cuttings must be held in suspension in the event of shut-downs in drilling.

An ideal drilling fluid is a thixotropic system. That is, the drilling fluid (1) will exhibit low viscosity when sheared, such as during agitation or circulation (as by pumping or otherwise) but, (2) when the shearing action is halted, the fluid must gel to hold the cuttings in place, and it must become gelled relatively rapidly, reaching a sufficient gel strength before suspended materials fall any significant distance, and (3) this behavior should be almost completely reversible. In addition, even when it is a free-flowing liquid, the fluid must retain a sufficiently high viscosity to carry all unwanted particulate matter from the bottom of the hole to the surface. Moreover, upon long-term interruption of circulation, such as when drilling fluid has been ejected from the borehole into a quiescent holding vessel or pond, the gel structure should remain intact to allow the weighting agent particles to remain suspended and maintain a uniform distribution throughout the fluid.

During the drilling process, some of the drilled solids erode and become finer particles that cannot be removed via solids control equipment (at the surface) due to their small size. As drilling progresses these particles become finer to colloidal size and increase in their concentration in the drilling fluid. These colloidal fines and their concentration can negatively impact the performance of the invert emulsion fluid (IEF). The performance of the IEF can be gauged by the American Petroleum Institute (API) fluid loss test, rheology and monitoring for emulsion stability. These colloidal fines can either cause an increase in the API fluid loss, increase the overall rheology of the fluids or at the very end may even destabilize the IEF. This increase in the overall rheology of the fluid can be determined by an increase in Fann 35 rheometer readings from 600 rotations per minute (rpm) to 3 rpm. An increase in overall rheology of the fluid increases the equivalent circulating density (ECD) of the fluid. The ECD is the effective density of the circulating fluid in the wellbore resulting from the sum of the hydrostatic pressure imposed by the static fluid column and the friction pressure. API STD 65—Part 2, Isolating Potential Flow Zones During Well Construction, Upstream Segment, Second Edition, December 2010. Global Standards. More specifically, an increase in the rheology increases the frictional pressure component in the ECD equation, and thereby, the ECD of the fluid. The ECD is an important parameter in avoiding kicks and losses of the fluid, particularly in wells that have a narrow window between the fracture gradient and pore-pressure gradient.

When the colloidal fines in the IEF increase, the fluid may be treated in one or more of the following ways, for example, by: (i) adding a thinner to lower the rheology; (ii) adding wetting agents to maintain the water wettability of the colloidal fines; (iii) adding fresh IEF to dilute the overall drilling fluid to reduce the overall concentration of the low gravity solids (LGS); (iv) performing high speed centrifuge operations to remove the finer solids; and/or (v) adding other additives to maintain a workable fluid. However, at times these treatments may not work and the whole of the used IEF has to be discarded and fresh IEF made.

It is therefore advantageous to have emulsifiers or additives as part of the IEF that reduce the maintenance/treatments of these fluids by maintaining controlled (low) rheology profile and API fluid loss performance of the IEF. This improvement will in turn increase the overall working longevity of the IEF. Thus, there is a need for a cost effective drilling fluid that can perform all the above mentioned functions. The present disclosure provides a drilling fluid with an IEF composition having low titer low titer fatty acid material (or low titer rosin acid containing fatty acid material) based specialty emulsifier which delivers a low rheology IEF even in the presence of a high concentration of low gravity solids (LGS). A low rheology in turn leads to lower induced fluid losses in the drilling fluid formation when drilling oil and gas wells.

SUMMARY

The present disclosure provides a low gravity solids (LGS) tolerant emulsifier, maleated low titer fatty acid material, or low titer rosin containing fatty acid material based amido-amine (herein, "MDTA") emulsifier, an invert emulsion fluid (herein, "IEF") comprising the MDTA emulsifier (i.e., the LGS tolerant emulsifier) of the present disclosure, drilling fluids comprising the IEF of the present disclosure, and associated methods of use. Surprisingly and unexpectedly, when incorporated into IEF compositions, the emulsifier of the present disclosure reduces IEF rheology even in the presence of a high LGS concentration—i.e. the IEF has a lower rheology as compared to an IEF without the MDTA emulsifier of the present disclosure. The low rheology in turn leads to lower induced fluid losses in the drilling fluid formation when drilling oil and gas wells.

Thus, in an aspect, the present disclosure provides a LGS tolerant emulsifier or MDTA emulsifier comprising a maleated amido-amine reaction product. The maleated amido-amine reaction product can be produced by: reacting a low titer fatty acid material (e.g., a lower titer fatty acid material comprising rosin acid) and an amine material to produce an amido-amine reaction product (or amido-amine intermediate reaction product or amido-amine low-titer fatty acid material intermediate reaction product or amido-amine low-titer rosin acid containing fatty acid material intermediate reaction product), and reacting the amido-amine reaction product with maleic anhydride to produce the maleated amido-amine reaction product.

In another aspect, the present disclosure provides methods for preparing/making a LGS tolerant emulsifier or a MDTA emulsifier. The method comprises: reacting a low titer fatty acid material (i.e., a low titer fatty acid material comprising rosin acid) and an amine material to produce an amido-amine low-titer fatty acid material intermediate (or amido-amine reaction product or amido-amine intermediate reaction product); and reacting the amido-amine low-titer fatty acid material intermediate or reaction product with maleic anhydride (e.g., adding maleic anhydride) to produce a maleated amido-amine reaction product or MDTA emulsifier. In certain embodiments, the method of preparing a MDTA emulsifier comprises reacting low titer fatty acid material (i.e., low titer rosin acid containing fatty acid material) and an amine resulting in an amido-amine-low titer fatty acid material intermediate; and reacting the intermediate with maleic anhydride (i.e., maleic anhydride addition) to form the LGS tolerant emulsifier or MDTA emulsifier.

In any aspect or embodiment described herein, the LGS tolerant emulsifier or MDTA emulsifier includes at least one of: the low titer fatty acid material or low titer rosin acid containing fatty acid material is present in an amount of about 55 wt. % to about 95 wt. % (e.g., about 65 wt. % to about 75 wt. %) of the amido-amine reaction product; the amine material is present in an amount of about 5 wt. % to about 45 wt. % (e.g., about 25 wt. % to about 35 wt. %) of the amido-amine reaction product; the maleic anhydride is present in an amount of about 1 wt. % to about 20 wt. % (e.g., about 5 wt. % to about 13 wt. %) of the maleated amido-amine reaction product or the emulsifier; or a combination thereof.

In any of the aspects or embodiments described herein, the low titer fatty acid material (e.g., low titer fatty material comprising rosin acid or low titer rosin acid containing material) includes or is at least one of: a side stream from the crude tall oil (CTO) refining process collected as the bottoms product during the subsequent production of low rosin (<5%) and low Gardner Color index (<7.0) tall oil fatty acid (TOFA) from refinery columns during the distillation of crude tall oil (CTO); a mixture of a blend of the side stream and at least one of distilled tall oil, tall oil fatty acid, rosin, or a combination thereof; a product stream of the CTO refining process; a mixture or blend of TOFA and distilled tall oil; a mixture or blend of a distilled tall oil and rosin; a mixture or blend of TOFA and rosin; a disproportionated tall oil, a mixture of disproportionated tall oil and rosin, a mixture of disproportionated tall oil and TOFA, a mixture of disproportionated tall oil and distilled tall oil (DTO), or a combination thereof; or a combination thereof.

In any aspect or embodiment described herein, the low titer fatty acid material or low titer fatty acid material comprising rosin acid has at least one of: an acid number ranging from about 143 to about 200 mg/g; a rosin acid concentration of about 11% to about 50%; a titer point of less than about 14° C.; a PAN rosin acid concentration of less than or equal to about 50%; heavies present in an amount of less than or equal to about 40% of the low titer fatty acid material; a Gardner color index in a range from about 4.0 to about 17.0; or a combination thereof. For example, in certain embodiments, the low titer fatty acid material has an acid number in a range from about 155 to about 174 mg/g or about 143 to about 185 mg/g. In any aspect or embodiment described herein, the low titer fatty acid material has a Gardner color index in a range from 4 to about 14.7.

In any of the aspects or embodiments described herein, the amine HST has an amine value between about 700 mg/g and about 1300 mg/g (e.g., about 750 mg/g to about 900 mg/g or about 750 mg/g).

In any aspect or embodiment described herein, the amine material includes or is a distillation residuum bottom composition of a reaction product of monoethanolamine and ammonia in which piperazine distillate product has been recovered.

In any of the aspects or embodiments described herein, the amine material includes or is a chemical composition with the Chemical Abstracts Service Registry No. 68910-05-4. For example, in certain embodiments, the amine material is or includes at least one of AMINE HST from Dow Chemical Co. (Midland, Mich.), AMIX 1000 from BASF (Ludwigshafen, Germany), Berolamine 20 (BA-20; AkzoNobel, Illinois Chicago), or a combination thereof.

In particular embodiments, the amine material includes or is a distillation residuum bottom composition of a reaction product of monoethanolamine and ammonia in which piperazine distillate product has been recovered.

In any aspect or embodiment described herein, the amine material includes at least one of: diethylenetriamine (DETA), hydroxyethyldiethylenetriamine (HEDETA), 2-piperazinoethanol, triethylenetetramine (TETA), Tetraethylenepentamine mixtures (TEPA), pentaethylene hexamine (PEHA) heptaethyleneoctamine (HEOA), hexaethyleneheptamine (HEHA), amine HST, amine DCT, aminoethylpiperazine (AEP), dimethylaminopropylamine (DMAPA), aminoethylethanolamine (AEEA), diethanolamine (DEA), triethanolamine (TEA), monoethanolamine, other higher ethylene amines, or combinations thereof.

In an embodiment, the amine material is or includes a chemical composition with the Chemical Abstract Service Registry No. 68910-05-4 (e.g., AMINE HST from Dow Chemical Co., AMIX 1000 from BASF, BA-20 from Akzo Nobel, or a combination thereof).

In certain embodiments, the amine material includes at least one of: AMINE HST from Dow Chemical Co., AMIX 1000 from BASF, BA-20 from Akzo Nobel, or a combination thereof.

In any aspect or embodiment described herein, the amido-amine reaction product (i.e., the amido-amine reaction intermediate product or amido-amine low-titer fatty acid material intermediate reaction product) includes at least one of amidoamines, alkanolamides, di-amidoamine, di-ester alcohol amine, ester alcohol amine, di-ester amine, ester amido amines, amido amine alcohols, amides of the hydroxy piperazine, amide imidazoline, ester imidazoline, amine imidazoline, alkanol imidazoline or combinations thereof.

In an additional aspect, the present disclosure provides an invert emulsion fluid (IEF) comprising the LGS tolerant emulsifier or MDTA emulsifier of the present disclosure, and at least one of a non-aqueous continuous phase, a discontinuous hygroscopic phase like brine, an additive, or a combination thereof. The IEF of the present disclosure, which includes the LGS tolerant emulsifier or MDTA emulsifier of the present disclosure, demonstrates controlled (i.e., reduced) rheology even in the presence of relatively high concentration of LGS, as compared to a maleated TOFA amido-amine (herein, "MHTA") emulsifier, which is generally recognized as the industry standard. See, for example, an emulsifier as disclosed in U.S. Pat. No. 8,927,468 B2, which is incorporated herein, as well as non-spray dried version thereof.

In any aspect or embodiment described herein, the IEF comprises between about 4 and about 12 V/V of LGS. In any aspect or embodiment described herein, the LGS have specific gravity between about 2.0 and about 3.0.

In any aspect or embodiment described herein, the IEF of the present disclosure has a low high temperature, high pressure (HTHP) fluid loss between about 1 and about 20 ml at 350° F. See, American Petroleum Institute (API) Recommended Practice 13B-2, Fourth Edition, Recommended Practice for Field Testing of Oil-based Drilling Fluids, for an exemplary test method to conduct the HTHP filtration test at the test temperature indicated above.

In any aspect or embodiment described herein, the IEF has a lower rheology than an IEF without the MDTA emulsifier (e.g., an IEF comprising a maleated TOFA amido-amine emulsifier).

In any aspect or embodiment described herein, the MDTA emulsifier of the present disclosure reduces the IEF rheology by from about 10 to about 92% (e.g., about 25 to about 85% or about 50 to about 85%), as compared to an IEF comprising a MHTA emulsifier (i.e., the industry standard). In any aspect or embodiment described herein, the IEF of the present disclosure has a low rheology having 600 rpm to 3 rpm dial readings that are lower than similarly formulated IEF with a MHTA emulsifiers at 150° F. In any aspect or embodiment described herein, the relative rheology may be determined at 100 ppb loading REVDUST® tested under standard conditions (e.g., an exemplary test method/conditions can be found at API Recommended Practice 13B-2, Fourth Edition, Recommended Practice for Field Testing of Oil-based Drilling Fluids).

In any aspect or embodiment described herein, the IEF of the present disclosure has a gel strength that is about 10 to about 92% (e.g., about 25 to about 85% or about 50 to about 85%) lower than a similarly formulated IEF without the described MDTA emulsifier (e.g., a similarly formulated IEF with a maleated TOFA amine emulsifier) at 150° F. In any aspect or embodiment described herein, the gel strength may be determined by API Recommended Practice 13B-2, Fourth Edition, Recommended Practice for Field Testing of Oil-based Drilling Fluids.

In any aspect or embodiment described herein, the IEF of the present disclosure has a low rheology having yield stress (Tau0) less than the yield stress of similarly formulated IEF without the described MDTA emulsifier (e.g., a similarly formulated IEF comprising a MHTA emulsifier) at 150° F.

In any aspect or embodiment described herein, the IEF of the present disclosure is used for gas and oil drilling.

In a further aspect, the present disclosure provides a drilling fluid comprising the IEF of the present disclosure (i.e., an IEF comprising the MDTA emulsifier of the present disclosure).

A further aspect of the present disclosure provides a method of drilling a well. The method comprises drilling a well bore and circulating the drilling fluid of the present disclosure through said well bore when drilling the well bore.

Further aspects, features, and advantages of the present disclosure will be apparent to those of ordinary skill in the art upon examining and reading the following Detailed Description of the Preferred Embodiments.

BRIEF DESCRIPTION OF THE FIGURES

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention. Further objects, features and advantages of the invention will become apparent from the following detailed description taken in conjunction with the accompanying figures showing illustrative embodiments of the invention, in which.

DETAILED DESCRIPTION

Figure 1:
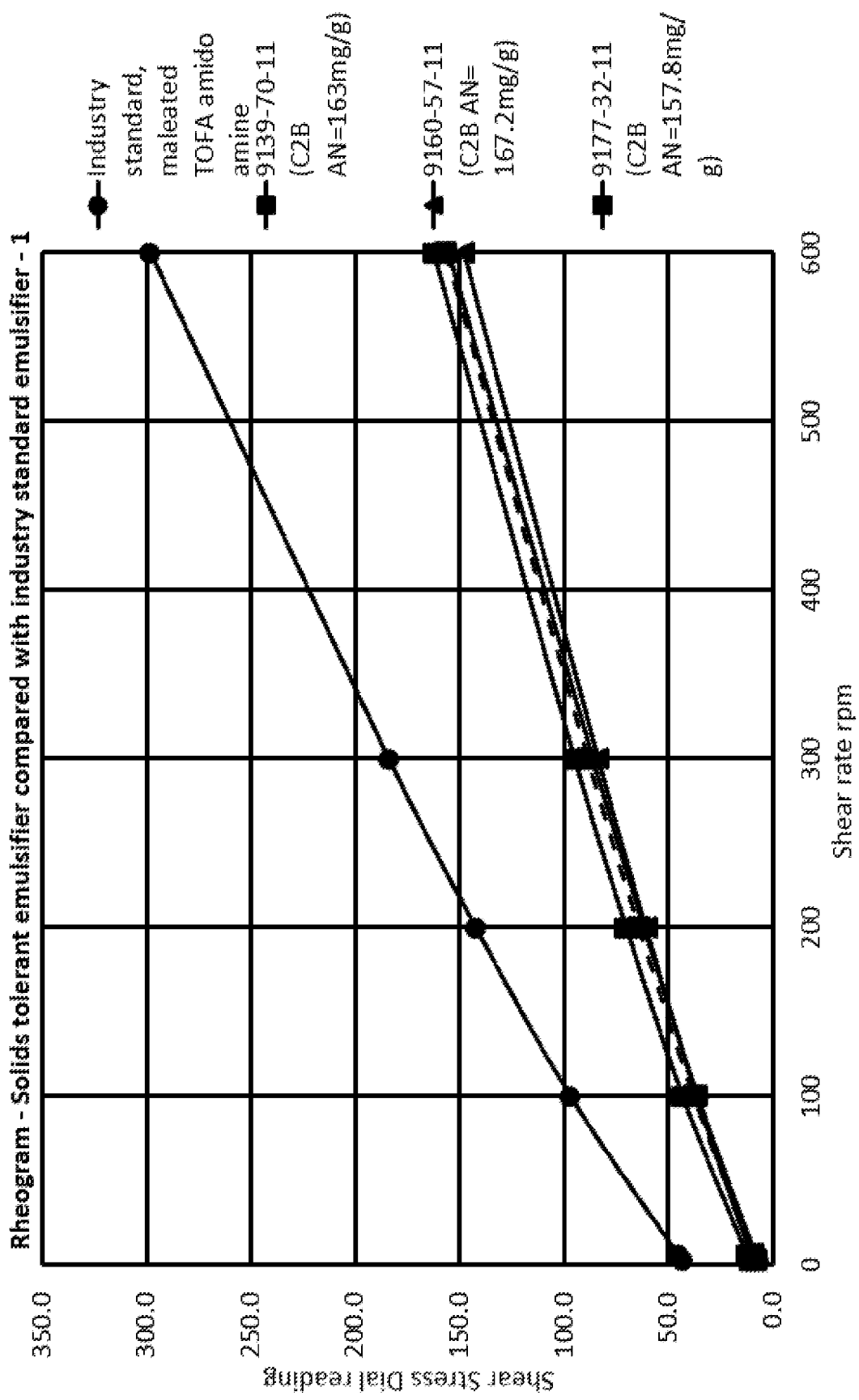
FIG. 1 is a graph illustrating shear stress relative to shear rate of exemplary solids tolerant emulsifiers and maleated TOFA amido-amine emulsifier.

The following is a detailed description provided to aid those skilled in the art in practicing the present disclosure. Those of ordinary skill in the art may make modifications and variations in the embodiments described herein without departing from the spirit or scope of the present disclosure. All publications, patent applications, patents, figures and other references mentioned herein are expressly incorporated herein by reference in their entirety for all purposes.

The present description provides improved compositions and methods for drilling wells, fracturing subterranean formations, and other treatments. The drilling and fracturing compositions and methods of the present disclosure are economical and desirable properties that are surprising and unexpected. In particular, the present disclosure provides a low gravity solids (LGS) tolerant emulsifier or maleated low titer fatty acid material (also referred to herein as a low titer fatty acid material comprising rosin acid or a low titer rosin acid containing fatty acid material) based amido-amine (herein, "MDTA") emulsifier, invert emulsion fluid (herein, "IEF") comprising the LGS tolerant emulsifier or MDTA emulsifier of the present disclosure, drilling fluids comprising the IEF of the present disclosure, and associated methods of use of each. Surprisingly and unexpectedly, when the LGS tolerant emulsifier or MDTA emulsifier of the present disclosure is incorporated into IEF compositions, the rheology of the IEF is reduced, even in the presence of a high LGS concentration—i.e. the IEF of the present disclosure has a lower rheology as compared to an IEF formulated with a conventional MHTA emulsifier (i.e., without the emulsifier of the present disclosure). The low rheology in turn leads to lower induced fluid losses in the drilling fluid formation when drilling oil and gas wells Unless otherwise defined, all technical and scientific terms used herein have the same meaning as commonly understood by one of ordinary skill in the art to which this disclosure belongs. The terminology used in the description is for describing particular embodiments only and is not intended to be limiting of the disclosure.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either both of those included limits are also included in the disclosure.

The following terms are used to describe the present disclosure. Unless otherwise defined, all technical and scientific terms used herein have the same meaning as commonly understood by one of ordinary skill in the art to which this disclosure belongs. The terminology used in the description is for describing particular embodiments only and is not intended to be limiting of the disclosure.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

As used herein, the term "drilling" or "drilling well bores" shall be understood in the broader sense of drilling operations, which include running casing and cementing as well as drilling, unless specifically indicated otherwise. The present disclosure also provides invert emulsion based drilling fluids for use in the methods of the disclosure to effect the advantages of the disclosure.

The present disclosure provides an invert emulsion drilling fluid that meets environmental constraints and provides improved performance in the field.

As disclosed herein, a "gel" may be defined a number of ways. One definition indicates that a "gel" is a generally colloidal suspension or a mixture of microscopic water particles (and any hydrophilic additives) approximately uniformly dispersed through the oil (and any hydrophobic additives), such that the fluid or gel has a generally homogeneous gelatinous consistency. Another definition states that a "gel" is a colloid in a more solid form than a "sol", which is a fluid colloidal system, especially one in which the continuous phase is a liquid. Still another definition provides that a "gel" is a colloid in which the disperse phase has combined with the continuous phase to produce a viscous jelly-like product. Generally, a gel has a structure that is continually building. If the yield stress of a fluid increases over time, the fluid has gelled. "Yield stress" is the stress required to be exerted to initiate deformation.

During drilling, the fluids of the present disclosure generally maintain consistently low values for the difference in their surface density and downhole equivalent circulating density (ECD), as well as have significantly reduced fluid loss, as compared to other (e.g., conventional) drilling fluids used under comparable conditions.

Oil or synthetic fluid-based muds are normally used to drill swelling or sloughing shales, salt, gypsum, anhydrite or other evaporate formations, hydrogen sulfide-containing formations, and hot boreholes (e.g. greater than about 300° F.) holes, but may be used in other holes penetrating a subterranean formation as well. Unless indicated otherwise, the terms "oil mud" or "oil-based mud or drilling fluid" shall be understood to include synthetic oils or other synthetic fluids as well as natural or traditional oils, and such oils shall be understood to comprise invert emulsions.

Oil-based muds used in drilling typically comprise: a base oil (e.g. natural or synthetic fluid) comprising the external phase of an invert emulsion; a saline, aqueous solution (e.g. an aqueous solution comprising about 20 to about 40% calcium chloride, or about 25% to about 35% calcium chloride, or about 30% calcium chloride) comprising the internal phase of the invert emulsion; emulsifiers at the interface of the internal and external phases; and other agents or additives for suspension, weight or density, oil-wetting, fluid loss or filtration control, and rheology control. Such additives commonly include organophilic clays and organophilic lignites. See H. C. H. Darley and George R. Gray, Composition and Properties of Drilling and Completion Fluids 66-67, 561-562 (5th ed. 1988). In any aspect or embodiment described herein, the oil-based or invert emulsion-based drilling fluid comprises between about 50:50 to about 95:5 by volume oil phase to water phase. In some embodiments, the drilling fluid is a completely oil mud simply comprises 100% liquid phase oil by volume; that is, there is no aqueous internal phase.

Invert emulsion drilling fluids (also called invert drilling muds or invert muds or fluids) comprise a key segment of the drilling fluids industry. However, increasingly invert emulsion-based drilling fluids have been subjected to greater environmental restrictions, as well as performance and cost demands. There is consequently an increasing need and industry-wide interest in new drilling fluids that provide improved performance while still affording environmental and economical acceptance. Furthermore, the automotive and metalworking industries are always looking for low cost, highly efficient lubricants and lubricant additives that are environmentally friendly and that have a high thermal stability. Many lubricants and lubricant additives currently used, e.g., in these industries, do not meet these performance criteria. In addition, most of them are petroleum-based and thus, non-renewable.

The compositions of the present disclosure relate to drilling fluid additives (e.g., a LGS tolerant emulsifier or MDTA emulsifier) and drilling fluids, which are also known as drilling muds in the oil service industry, that have surprising and unexpected improvements in low gravity solids tolerance, while maintaining controlled (low) rheology. In particular, the compositions of the present disclosure relate to oil and invert oil based emulsion types of drilling fluids in which water is dispersed in an oil-based medium. Such drilling fluid compositions when prepared at a mud plant are often called mud plant formulations. The disclosure is particularly directed to providing an invert emulsion fluid with low rheology and that is tolerant to high concentrations of low gravity solids.

Maleated Low Titer Fatty Acid Material Based Amine Emulsifier

An aspect of the present disclosure provides a low gravity solid (LGS) tolerant emulsifier or MDTA emulsifier. The emulsifier of the present disclosure includes a maleated amido-amine reaction product produced by reacting a low titer fatty acid material (e.g., a low titer fatty acid material comprising rosin acid or low titer rosin acid containing fatty acid material) with an amine material to produce an amido-amine low-titer fatty acid material intermediate reaction product (or amido-amine intermediate product or amido-amine reaction product), and reacting the amido-amine low-titer fatty acid material intermediate reaction product with maleic anhydride to produce the maleated amido-amine reaction product. The reaction conditions like temperature and hold time at the highest temperature are specially engineered to derive maximum LGS tolerance. As used herein, unless the context indicates otherwise, the term low titer fatty acid material amido-amine is used inclusively of bis-amide amine, amido amines, alkanol amides, ester amido amines, amido amine alcohols, amides of the hydroxy piperazine, produced according to the methods described herein from the reaction of a low titer fatty acid material with an amine source.

In any aspect or embodiment described herein, the low titer fatty acid material or low titer rosin acid containing fatty acid material comprises about 55 wt. % to about 95 wt.

% of the amido-amine reaction product. For example, in certain embodiments, the low-titer fatty acid material is present in an amount of about 55 wt. % to about 95 wt. %, about 55 wt. % to about 90 wt. %, about 55 wt. % to about 85 wt. %, about 55 wt. % to about 80 wt. %, about 55 wt. % to about 75 wt. %, about 55 wt. % to about 70 wt. %, about 55 wt. % to about 65 wt. %, about 55 wt. % to about 60 wt. %, about 60 wt. % to about 95 wt. %, about 60 wt. % to about 90 wt. %, about 60 wt. % to about 85 wt. %, about 60 wt. % to about 80 wt. %, about 60 wt. % to about 75 wt. %, about 60 wt. % to about 70 wt. %, about 60 wt. % to about 65 wt. %, about 65 wt. % to about 95 wt. %, about 65 wt. % to about 90 wt. %, about 65 wt. % to about 85 wt. %, about 65 wt. % to about 80 wt. %, about 65 wt. % to about 75 wt. %, about 65 wt. % to about 70 wt. %, about 70 wt. % to about 95 wt. %, about 70 wt. % to about 90 wt. %, about 70 wt. % to about 85 wt. %, about 70 wt. % to about 80 wt. %, about 70 wt. % to about 75 wt. %, about 75 wt. % to about 95 wt. %, about 75 wt. % to about 90 wt. %, about 75 wt. % to about 85 wt. %, about 75 wt. % to about 80 wt. %, about 80 wt. % to about 95 wt. %, about 80 wt. % to about 90 wt. %, about 80 wt. % to about 85 wt. %, about 85 wt. % to about 95 wt. %, about 85 wt. % to about 90 wt. %, or about 90 wt. % to about 95 wt. %, of the amido-amine reaction product. In any aspect or embodiment described herein, the low titer fatty acid material or low titer rosin acid containing fatty acid material is present in an amount of about 55 wt. %, about 56 wt. %, about 57 wt. %, about 58 wt. %, about 59 wt. %, about 60 wt. %, about 61 wt. %, about 62 wt. %, about 63 wt. %, about 64 wt. %, about 65 wt. %, about 66 wt. %, about 67 wt. %, about 68 wt. %, about 69 wt. %, about 70 wt. %, about 71 wt. %, about 72 wt. %, about 73 wt. %, about 74 wt. %, about 75 wt. %, about 76 wt. %, about 77 wt. %, about 78 wt. %, about 79 wt. %, about 80 wt. %, about 81 wt. %, about 82 wt. %, about 83 wt. %, about 84 wt. %, about 85 wt. %, about 86 wt. %, about 87 wt. %, about 88 wt. %, about 89 wt. %, about 90 wt. %, about 91 wt. %, about 92 wt. %, about 93 wt. %, about 94 wt. %, or about 95 wt. % of the amido-amine reaction product.

In any aspect or embodiment described herein, the amine material (or mixture of amines) is present in an amount of about 5 wt. % to about 45 wt. % of the amido-amine reaction product. For example, in certain embodiments, the amine or amines is/are present in an amount of about 5 wt. % to about 45 wt. %, about 5 wt. % to about 40 wt. %, about 5 wt. % to about 35 wt. %, about 5 wt. % to about 30 wt. %, about 5 wt. % to about 25 wt. %, about 5 wt. % to about 20 wt. %, about 5 wt. % to about 15 wt. %, about 10 wt. % to about 45 wt. %, about 10 wt. % to about 40 wt. %, about 10 wt. % to about 35 wt. %, about 10 wt. % to about 30 wt. %, about 10 wt. % to about 25 wt. %, about 10 wt. % to about 20 wt. %, about 15 wt. % to about 45 wt. %, about 15 wt. % to about 40 wt. %, about 15 wt. % to about 35 wt. %, about 15 wt. % to about 30 wt. %, about 15 wt. % to about 25 wt. %, about 20 wt. % to about 45 wt. %, about 20 wt. % to about 40 wt. %, about 20 wt. % to about 35 wt. %, about 20 wt. % to about 30 wt. %, about 25 wt. % to about 45 wt. %, about 25 wt. % to about 40 wt. %, about 25 wt. % to about 35 wt. %, about 30 wt. % to about 45 wt. %, about 30 wt. % to about 40 wt. %, or about 35 wt. % to about 45 wt. % of the amido-amine reaction product. In any aspect or embodiments described herein, the amine or combination of amines is present in an amount of about 5 wt. %, 6 wt. %, 7 wt. %, 8 wt. %, 9 wt. %, 10 wt. %, 11 wt. %, 12 wt. %, 13 wt. %, 14 wt. %, 15 wt. %, 16 wt. %, 17 wt. %, 18 wt. %, 19 wt. %, 20 wt. %, 21 wt. %, 22 wt. %, 23 wt. %, 24 wt. %, about 25 wt. %, about 26 wt. %, about 27 wt. %, about 27 wt. %, about 28 wt. %, about 29 wt. %, about 30 wt. %, about 31 wt. %, about 32 wt. %, about 33 wt. %, about 34 wt. %, about 35 wt. %, about 36 wt. %, about 37 wt. %, about 38 wt. %, about 39 wt. %, about 40 wt. %, about 41 wt. %, about 42 wt. %, about 43 wt. %, about 44 wt. %, or about 45 wt. % of the amido-amine reaction product.

In any aspect or embodiment described herein, the maleic anhydride comprises about 1 wt. % to about 20 wt. % of the maleated amido-amino reaction product or the emulsifier composition. For example, in certain embodiments, the maleic anhydride is present in an amount of about 1 wt. % to about 20 wt. %, about 2.5 wt. % to about 20 wt. %, about 5 wt. % to about 20 wt. %, about 7.5 wt. % to about 20 wt. %, about 10 wt. % to about 20 wt. %, about 12.5 wt. % to about 20 wt. %, about 15 wt. % to about 20 wt. %, about 17.5 wt. % to about 20 wt. %, about 1 wt. % to about 17.5 wt. %, about 2.5 wt. % to about 17.5 wt. %, about 5 wt. % to about 17.5 wt. %, about 7.5 wt. % to about 17.5 wt. %, about 10 wt. % to about 17.5 wt. %, about 12.5 wt. % to about 17.5 wt. %, about 15 wt. % to about 17.5 wt. %, about 1 wt. % to about 15 wt. %, about 2.5 wt. % to about 15 wt. %, about 5 wt. % to about 15 wt. %, about 7.5 wt. % to about 15 wt. %, about 10 wt. % to about 15 wt. %, about 12.5 wt. % to about 15 wt. %, about 1 wt. % to about 15 wt. %, about 2.5 wt. % to about 15 wt. %, about 5 wt. % to about 15 wt. %, about 7.5 wt. % to about 15 wt. %, about 10 wt. % to about 15 wt. %, about 12.5 wt. % to about 15 wt. %, about 1 wt. % to about 12.5 wt. %, about 2.5 wt. % to about 12.5 wt. %, about 5 wt. % to about 12.5 wt. %, about 7.5 wt. % to about 12.5 wt. %, about 10 wt. % to about 12.5 wt. %, about 1 wt. % to about 10 wt. %, about 2.5 wt. % to about 10 wt. %, about 5 wt. % to about 10 wt. %, about 7.5 wt. % to about 10 wt. %, about 1 wt. % to about 7.5 wt. %, about 2.5 wt. % to about 7.5 wt. %, about 5 wt. % to about 7.5 wt. %, about 1 wt. % to about 5 wt. %, about 2.5 wt. % to about 5 wt. %, or about 2.5 wt. % to about 5 wt. % of the maleated amido-amine reaction product or the emulsifier composition. In any aspect or embodiment described herein, the maleic anhydride is present in an amount of about 1 wt. %, about 2 wt. %, about 3 wt. %, about 4 wt. %, about 5 wt. %, about 6 wt. %, about 7 wt. %, about 8 wt. %, about 9 wt. %, about 10 wt. %, about 11 wt. %, about 12 wt. %, about 12 wt. %, about 13 wt. %, about 14 wt. %, about 16 wt. %, about 17 wt. %, about 18 wt. %, about 19 wt. %, or about 20 wt. % of the maleated amido-amine reaction product or the emulsifier composition.

Low Titer Fatty Acid Material

In any aspects or embodiment described herein, the low titer fatty acid material, low titer fatty acid material comprising rosin acid, or low titer rosin acid containing fatty acid material includes or is a side stream from the crude tall oil (CTO) refining process. For example, the low titer fatty acid material includes or is a side stream collected as the bottoms product during the subsequent production of low rosin (<5%) and low Gardner Color index (<7.0) tall oil fatty acid (TOFA) from refinery columns during the distillation of crude tall oil (CTO). For example, in any aspect or embodiment described herein, the side stream from the CTO refining process is C2-B° (available from Ingevity, Charleston, S.C.). Thus, in any aspect or embodiment described herein, the low titer fatty acid material is or includes a side stream from the CTO refining process that has at least one of: an acid number of about 143 mg/g to about 185 mg/g (e.g., about 155 mg/g to about 174 mg/g) or about 150 mg/g to about 200 mg/g, about 12% to about 40% rosin acids, a titer point of less than −2° C., about 45% fatty acids, about 14% monounsaturated fatty acids, about 34% unsaturated fatty acids, less than about 3% saturated fatty acids, or a combination thereof.

In any aspect or embodiment described herein, the low titer fatty acid material is or includes the side stream from the CTO refining process and at least one of distilled tall oil, tall oil fatty acid, rosin, or a combination thereof, wherein the rosin acid content of the low titer fatty acid material is as described herein.

In any aspect or embodiment described herein, the low titer fatty acid material is or includes a product stream of the CTO refining process, wherein the CTO refining process product stream has a rosin acid content as described herein. For example, in any aspect or embodiment described herein, the CTO refining process product stream is (1) Altapyne™ M-28B (e.g., about 26 to about 30% or about 28% rosin acid content) (Ingevity Corp., Charleston, S.C.); (2) a distilled tall oil having at least one of about 11% to about 12% rosin acid, an acid number of less than or equal to about 188 mg/g, a Gardner Color Index of less than or equal to about 8, less than or equal to about 1% palmitic acid, a titer point of less than about 14° C., or a combination thereof; or (3) a combination thereof. Thus, in any aspect or embodiment described herein, the low titer fatty acid material is or includes (1) a distilled tall oil having at least one of: about 26% to about 30% rosin acid, an acid number of at least about 180 mg/g, a Gardner Color Index of less than or equal to 10, a titer point of about 10° C. to about 12° C. (e.g., about 11° C.), or a combination thereof; (2) a distilled tall oil having at least one of about 11% to about 12% rosin acid, an acid number of less than or equal to about 188 mg/g, a Gardner Color Index of less than or equal to about 8, less than or equal to about 1% palmitic acid, a titer point of less than about 14° C., or a combination thereof; or (3) a combination thereof.

In any aspect or embodiment described herein, the low titer fatty acid material is or includes one or more distilled tall oils (e.g., 1, 2, 3, 4, 5, 6, or more distilled tall oils). For example, in any aspect or embodiment described herein, the distilled tall oil is or includes at least one of: Altapyne™ M-50B (about 45.0 to about 48.5% rosin acid content), Altapyne™ M-25 (about 12.0 to about 40.0% rosin acid content), Altapyne™ M-38 (about 37.0 to about 43.0% rosin acid content), Altapyne™ M-226 (about 25.0 to about 28.0% rosin acid content), or a combination thereof. Thus, in any aspect or embodiment described herein, the low titer fatty acid material is or includes a distilled tall oil having at least one of an acid number of about 175 mg/g to about 180 mg/g, about 45 to about 48.5% rosin acid, a Gardner Color Index of no greater than about 17 (e.g., about 17), or a combination thereof. In any aspect or embodiment described herein, the low titer fatty acid material is or includes a distilled tall oil having at least one of: an acid number of about 150 mg/g to about 200 mg/g, about 12.0 to about 40.0% rosin acid (e.g., about 20% rosin acid), a Gardner Color Index of about 10 to about 12 (e.g., about 11), a titer point of less than or equal to −2° C., about 45% fatty acids, less than about 3% saturated fatty acids, about 14% monosaturated fatty acids, about 34% unsaturated fatty acids, or a combination thereof. In any aspect or embodiment described herein, the low titer fatty acid material is or includes a distilled tall oil having at least one of: an acid number of about 175 mg/g to about 200 mg/g, about 37.0 to about 43.0% rosin acid (e.g., about 40% rosin acid), a Gardner Color Index equal to or less than 9 (e.g., about 7 to about 9), or a combination thereof. In any aspect or embodiment described herein, the low titer fatty acid material is or includes a distilled tall oil having at least one of: an acid number of about 182.0 mg/g to about 200 mg/g (e.g., about 189 mg/g), about 25.0 to about 28.0% rosin acid (e.g., about 26% rosin acids), a Gardner Color Index of equal to or less than 7 (e.g., about 5 to about 7 or about 6), about 1.0% or less palmitic acid, about 6.0% or less pimaric acid, or a combination thereof.

In any aspect or embodiment described herein, the low titer fatty acid material is or includes a mixture or blend of tall oil fatty acid and distilled tall oil, wherein the low titer fatty acid material has a rosin acid content as described herein. For example, in any aspect or embodiment described herein, the blend or mixture of tall oil fatty acid and distilled tall oil fatty acid is or includes Altapyne™ M-15 (about 10% to about 15% or about 13% rosin acid content) (Ingevity Corp., Charleston, S.C.). Thus, in any aspect or embodiment described herein, the low titer fatty acid material includes or is a distilled tall oil having at least one of: about 10 to about 15% rosin acid, an acid number of about 175 mg/g to about 195 mg/g, a Gardner Color Index equal to or less than 10, a titer point of about 9 to about 11° C. (such as about 10° C.), or a combination thereof.

In any aspect or embodiment described herein, the low titer fatty acid material is or includes a mixture or blend of distilled tall oil and rosin, wherein the low titer fatty acid material has a rosin acid content as described herein. For example, in any aspect or embodiment described herein, the blend or mixture of distilled tall oil and rosin is or includes Altapyne™ M-32 (about 30% to about 34% or about 30% rosin acid) (Ingevity Corp., Charleston, S.C.). Thus, in any aspect or embodiment described herein, the low titer fatty acid material includes or is a distilled tall oil having at least one of: about 30% to about 34% rosin acid, an acid number of about 170 mg/g to about 185 mg/g, a Gardner Color Index of less than or equal to 12, a titer point of about 10 to about 12° C. (such as about 11° C.), or a combination thereof.

In any aspect or embodiment described herein, the low titer fatty acid material is or includes a mixture or blend of TOFA and rosin, wherein the rosin acid content is as described herein. For example, in any aspect or embodiment described herein, the blend or mixture of TOFA and rosin is or includes Altapyne™ M-30D (e.g., about 26% to about 31% rosin acid) (Ingevity Corp., Charleston, S.C.). Thus, in any aspect or embodiment described herein, the low titer fatty acid material includes or is a blend or mixture of TOFA and rosin, wherein the low titer fatty acid material includes or is a blend or mixture of TOFA and rosin that has at least one of: about 26% to about 31% rosin acid, an acid number of about 180 mg/g to about 185 mg/g, about 64% to about 70% fatty acids, a Gardner Color Index equal to or less than 11, a titer point of about 8° C. to about 12° C., or a combination thereof.

In any aspect or embodiment described herein, the low titer fatty acid material is or includes a disproportionated tall oil, a mixture of disproportionated tall oil and rosin, a mixture of disproportionated tall oil and TOFA, a mixture of disproportionated tall oil and distilled tall oil (DTO), or a combination thereof, wherein the low titer acid material has a rosin acid content as described herein. For example, in any aspect or embodiment described herein, the low titer fatty acid material is or includes Altapyne™ 1430 (Ingevity Corp., Charleston, S.C.). Thus, in any aspect or embodiment described herein, the low titer fatty acid material is or includes a disproportionated tall oil, having at least one of: an acid number of about 170 to about 185 mg/g, about 24% to about 30% rosin acid, a Gardner Color Index of no greater than about 12, about 60% to about 70% fatty acids, about 30% to about 40% oleic acid, about 8 to about 30% dehydroabietic acid, less than about 1.0% abietic acid, or a combination thereof.

In any aspect or embodiment described herein, the low titer fatty acid material is or includes at least one of SYLVATAL™ D25LR (e.g., a DTO composition with an acid number of about 186 mg/g, about 70% fatty acids, about 26% rosin acids, titer point of about 2° C.; Arizona Chemicals, Jascksonville, Fla.), SYLVATAL™ D30LR (e.g., a DTO composition with an acid number of about 185 mg/g, about 66% fatty acids, about 30% rosin acids, titer point of about 2 to about 10° C. (e.g., about 10° C.); Arizona Chemicals, Jascksonville, Fla.), SYLFATAL™ D40LR (e.g., a DTO composition with an acid number of about 181 mg/g, about 58% fatty acids, about 39% rosin acids, titer point of about 2° C.; Arizona Chemicals, Jascksonville, Fla.), or a combination thereof.

In any aspect or embodiment described herein, the low titer fatty acid material, low titer fatty acid material comprising rosin acid, or low titer rosin acid containing fatty acid material has an acid number of about 143 to about 200 mg/g. For example, in any aspect or embodiment described herein, the low titer fatty acid material, low titer fatty acid material comprising rosin acid, or low titer rosin acid containing fatty acid material has an acid number of about 143 to about 200 mg/g, about 143 to about 195 mg/g, about 143 to about 190 mg/g, about 143 to about 185 mg/g, about 143 to about 185 mg/g, about 143 to about 175 mg/g, about 143 to about 170 mg/g, about 143 to about 165 mg/g, about 143 to about 160 mg/g, about 143 to about 155 mg/g, about 143 to about 150 mg/g, about 145 to about 200 mg/g, about 145 to about 195 mg/g, about 145 to about 190 mg/g, about 145 to about 185 mg/g, about 145 to about 180 mg/g, about 145 to about 175 mg/g, about 145 to about 170 mg/g, about 145 to about 165 mg/g, about 145 to about 160 mg/g, about 145 to about 155 mg/g, about 145 to about 150 mg/g, about 150 to about 200 mg/g, about 150 to about 195 mg/g, about 150 to about 190 mg/g, about 150 to about 185 mg/g, about 150 to about 180 mg/g, about 150 to about 175 mg/g, about 150 to about 170 mg/g, about 150 to about 165 mg/g, about 150 to about 160 mg/g, about 150 to about 155 mg/g, about 155 to about 200 mg/g, about 155 to about 195 mg/g, about 155 to about 190 mg/g, about 155 to about 185 mg/g, about 155 to about 180 mg/g, about 155 to about 175 mg/g, about 155 to about 170 mg/g, about 155 to about 165 mg/g, about 155 to about 160 mg/g, about 160 to about 200 mg/g, about 160 to about 195 mg/g, about 160 to about 190 mg/g, about 160 to about 185 mg/g, about 160 to about 180 mg/g, about 160 to about 175 mg/g, about 160 to about 170 mg/g, about 160 to about 165 mg/g, about 165 to about 200 mg/g, about 165 to about 195 mg/g, about 165 to about 190 mg/g, about 165 to about 185 mg/g, about 165 to about 180 mg/g, about 165 to about 175 mg/g, about 165 to about 170 mg/g, about 170 to about 200 mg/g, about 170 to about 195 mg/g, about 170 to about 190 mg/g, about 170 to about 185 mg/g, about 170 to about 180 mg/g, about 170 to about 175 mg/g, about 175 to about 185 mg/g, about 175 to about 180 mg/g, about 180 to about 200 mg/g, about 180 to about 195 mg/g, about 180 to about 190 mg/g, about 180 to about 185 mg/g, about 185 to about 200 mg/g, about 185 to about 195 mg/g, about 185 to about 190 mg/g, about 190 to about 200 mg/g, about 190 to about 195 mg/g, or about 195 to about 500 mg/g. In any aspect or embodiment described herein, the fatty acid material has an acid number of about 143, about 144, about 145, about 146, about 147, about 148, about 149, about 150, about 151, about 152, about 153, about 154, about 155, about 156, about 157, about 158, about 159, about 160, about 161, about 162, about 163, about 164, about 165, about 166, about 167, about 168, about 169, about 170, about 171, about 172, about 173, about 174, about 175, about 176, about 177, about 178, about 179, about 180, about 181, about 182, about 183, about 184, about 185, about 186, about 187, about 188, about 189, about 190, about 191, about 192, about 193, about 194, about 195, about 196, about 197, about 198, about 199, or about 200 mg/g.

In any aspect or embodiment described herein, acid number can be determined by titration. For example, in any aspect or embodiment described herein, acid number can be determined by titration with 0.5N KOH. An exemplary method to determine acid number through titration is described below in the Examples.

In any aspect or embodiment described herein, the low titer fatty acid material, low titer fatty acid material comprising rosin acid, or low titer rosin acid containing fatty acid material has a rosin acid (RA) concentration or content of about 11% to about 50% (e.g., about 11% to about 41% or about 19% to about 28%). For example, in any aspect or embodiment described herein, the RA concentration of the low titer fatty acid material is about 11% to about 50%, about 11% to about 45%, about 11% to about 41%, about 11% to about 35%, about 11% to about 30%, about 11% to about 25%, about 11% to about 20%, about 15% to about 50%, about 15% to about 45%, about 15% to about 41%, about 15% to about 35%, about 15% to about 30%, about 15% to about 25%, about 20% to about 50%, about 20% to about 45%, about 20% to about 41%, about 20% to about 35%, about 20% to about 30%, about 25% to about 50%, about 25% to about 45%, about 25% to about 41%, about 25% to about 35%, about 30% to about 50%, about 30% to about 45%, about 30% to about 41%, about 35% to about 50%, about 35% to about 45%, or about 40% to about 50%. The RA concentration can be determined by titration. For example, in certain embodiments, a modified Glidden procedure is utilized for RA concentration of about 15% or less, and for RA concentration of about 15% or greater a modified Wolfe Method is utilized. Alternatively, the RA concentration can be determined by the organic gel permeation chromatography. In any aspect or embodiment described herein, the rosin acid includes or is at least one of palustric acid, abietic acid, neoabietic acid, pimaric acid, levopimaric acid, isopimaric acid, a disproportionated rosin acid (e.g., dehydroabietic acid), or a combination thereof.

In any aspect or embodiment described herein, the low titer fatty acid material, low titer fatty acid material comprising rosin acid, or low titer rosin acid containing fatty acid material, is or includes a stream from the tall oil fatty acid distillation or processing (e.g., crude tall oil refining). In an embodiment, the low titer fatty acid material stream, low titer fatty acid material comprising rosin acid stream, or low titer rosin acid containing fatty acid material stream is or includes a by-product of crude tall oil refining process during the production of the light colored (Gardner color<7) highly pure TOFA (e.g., TOFA with a RA concentration of less than about 5% as determined by titration).

In any aspect or embodiment described herein, the low titer fatty acid material, low titer fatty acid material comprising rosin acid, or low titer rosin acid containing fatty acid material has a titer point<about 14° C. (e.g., <about 13° C., <about 12° C., <about 11° C., <about 10° C., <about 9° C., <about 8° C., <about 7° C., <about 6° C., <about 5° C., <about 4° C., <about 3° C., <about 2° C., or <about 1° C.). In any aspect or embodiment described herein, the fatty acid (FA) concentration can be in the range of about 34% to about 89% (e.g., about 34% to about 76% or about 40%-about 60%). For example, in any aspect or embodiment described herein, the fatty acid concentration in the low titer fatty acid material, low titer fatty acid material comprising rosin acid, or low titer rosin acid containing fatty acid material is about 34% to about 89%, about 34% to about 80%, about 34% to about 70%, about 34% to about 60%, about 34% to about 50%, about 34% to about 40%, about 40% to about 89%, about 40% to about 80%, about 40% to about 70%, about 40% to about 60%, about 40% to about 50%, about 50% to about 89%, about 50% to about 80%, about 50% to about 70%, about 50% to about 60%, about 60% to about 89%, about 60% to about 80%, about 60% to about 70%, about 70% to about 89%, about 70% to about 80%, or about 80% to about 89%. In any aspect or embodiment described herein, the low titer fatty acid material, low titer fatty acid material comprising rosin acid, or low titer rosin acid containing fatty acid material includes at least one of: C18 type fatty acids is present in an amount of about 25 to about 89% (e.g., about 25 to about 77%); C20 type fatty acids is present in an amount of less than or equal to about 34% (e.g., about 0.4 to about 34% or about 8 to about 34%), C16 type fatty acids is present in an amount of no greater than about 5% (e.g., no greater than about 4%, no greater than about 3%, no greater than about 2%; no greater than about 1%, or a combination thereof. For example, in any aspect or embodiment described herein, the low titer fatty acid material includes C18 fatty acids present in an amount of about 25 to about 89%, about 25 to about 80%, about 25 to about 70%, about 25 to about 60%, about 25 to about 50%, about 25 to about 40%, about 25 to about 35%, about 35 to about 89%, about 35 to about 80%, about 35 to about 70%, about 35 to about 60%, about 35 to about 50%, about 35 to about 45%, about 45 to about 89%, about 45 to about 80%, about 45 to about 70%, about 45 to about 60%, about 45 to about 55%, about 55 to about 89%, about 55 to about 80%, about 55 to about 70%, about 55 to about 65%, about 65 to about 89%, about 65 to about 80%, about 65 to about 75%, about 65 to about 89%, about 65 to about 80%, about 65 to about 75%, about 75 to about 89%, about 75 to about 85%, or about 80 to about 89%. In any aspect or embodiment described herein, the low titer fatty acid material includes C20 fatty acids present in an amount of ≤about 34%, ≤about 30%, ≤about 25%, ≤about 20%, ≤about 15%, ≤about 10%, ≤about 5%, about 0.4 to about 34%, about 0.4 to about 30%, about 0.4 to about 25%, about 0.4 to about 20%, about 0.4 to about 15%, about 0.4 to about 10%, about 0.4 to about 5%, about 5 to about 34%, about 5 to about 30%, about 5 to about 25%, about 5 to about 20%, about 5 to about 15%, about 5 to about 10%, about 10 to about 34%, about 10 to about 30%, about 10 to about 25%, about 10 to about 20%, about 10 to about 15%, about 15 to about 34%, about 15 to about 30%, about 15 to about 25%, about 15 to about 20%, about 20 to about 34%, about 20 to about 30%, about 20 to about 25%, about 25 to about 34%, about 25 to about 30%, or about 30 to about 35%. In any aspect or embodiment described herein, the titer point can be determined via ASTM D1982-61 or the exemplary method described in the Examples.

The fatty acid concentration and/or content can be determined by organic gel permeation chromatography (GPC), e.g., GPC using tetrahydrofuran (THF) as the mobile phase and refractive index detector. Since GPC alone cannot differentiate and estimate different carbon chain lengths in the fatty acid. Further determination of the fatty acid type and percentage is estimated by the combination of GPC and gas chromatography (GC) methods, wherein the correction factor for the heavies is determined by the GPC method. Thus, for example, from the GC method of analysis the fatty acid content, the low titer fatty acid material, low titer fatty acid material comprising rosin acid, or low titer rosin acid containing fatty acid material can include: predominantly C18 type fatty acid (e.g., about 25-about 89% or about 25-about 77%), less than or equal to about 34% (e.g., about 0.4 to about 34% or about 8 to about 34%) C20 type fatty acids; minor components of C16 type fatty acids (e.g., ≤about 5%, ≤about 4%, ≤about 3%, ≤about 2%, or about 0.5 to about 3%); or a combination thereof.

In any aspect or embodiment described herein, the fatty acid material or low titer fatty acid material, low titer fatty acid material comprising rosin acid, or low titer rosin acid containing fatty acid material comprises a PAN rosin acid (e.g., palustric, abietic, and/or the neoabietic acid) concentration or content of less than or equal to about 50% (e.g., about 0.25% to about 50%, less than or equal to about 11%, or about 0.25% to about 11%). For example, in any aspect or embodiment described herein, the PAN rosin acid concentration or content of the low titer fatty acid material, low titer fatty acid material comprising rosin acid, or low titer rosin acid containing fatty acid material is equal to or less than about 50%, equal to or less than about 45%, equal to or less than about 40%, equal to or less than about 35%, equal to or less than about 30%, equal to or less than about 25%, equal to or less than about 20%, equal to or less than about 15%, equal to or less than about 11%, less than or equal to about 10%, less than or equal to about 9%, less than or equal to about 8%, less than or equal to about 7%, less than or equal to about 6%, less than or equal to about 5%, less than or equal to about 4%, less than or equal to about 3%, about 0.25% to about 50%, about 0.25% to about 45%, about 0.25% to about 35%, about 0.25% to about 30%, about 0.25% to about 25%, about 0.25% to about 20%, about 0.25% to about 15%, about 0.25% to about 10%, about 0.25% to about 5%, about 5% to about 50%, about 5% to about 45%, about 5% to about 35%, about 5% to about 30%, about 5% to about 25%, about 5% to about 20%, about 5% to about 15%, about 5% to about 10%, about 10% to about 50%, about 10% to about 45%, about 10% to about 35%, about 10% to about 30%, about 10% to about 25%, about 10% to about 20%, about 10% to about 15%, about 15% to about 50%, about 15% to about 45%, about 15% to about 35%, about 15% to about 30%, about 15% to about 25%, about 15% to about 20%, about 20% to about 50%, about 20% to about 45%, about 20% to about 35%, about 20% to about 30%, about 20% to about 25%, about 25% to about 50%, about 25% to about 45%, about 25% to about 35%, about 25% to about 30%, about 30% to about 50%, about 30% to about 45%, about 30% to about 35%, about 35% to about 50%, about 35% to about 45%, about 35% to about 40%, about 40% to about 50%, about 40% to about 45%, about 45% to about 40%, about 0.25% to about 11%, about 0.25% to about 10%, about 0.25% to about 9%, about 0.25% to about 8%, about 0.25% to about 7%, about 0.25% to about 6%, about 0.25% to about 5%, about 0.25% to about 4%, about 0.25% to about 3%, about 1% to about 11%, about 1% to about 10%, about 1% to about 9%, about 1% to about 8%, about 1% to about 7%, about 1% to about 6%, about 1% to about 5%, about 1% to about 4%, about 1% to about 3%, about 2% to about 11%, about 2% to about 10%, about 2% to about 9%, about 2% to about 8%, about 2% to about 7%, about 2% to about 6%, about 2% to about 5%, about 2% to about 4%, about 3% to about 11%, about 3% to about 10%, about 3% to about 9%, about 3% to about 8%, about 3% to about 7%, about 3% to about 6%, about 3% to about 5%, about 4% to about 11%, about 4% to about 10%, about 4% to about 9%, about 4% to about 8%, about 4% to about 7%, about 4% to about 6%, about 5% to about 11%, about 5% to about 10%, about 5% to about 9%, about 5% to about 8%, about 5% to about 7%, about 6% to about 11%, about 6% to about 10%, about 6% to about 9%, about 6% to about 8%, about 7% to about 11%, about 7% to about 10%, about 7% to about 9%, about 8% to about 11%, about 8% to about 10%, or about 9% to about 11%. For example, in particular embodiments, the low titer fatty acid material, low titer fatty acid material comprising rosin acid, or low titer rosin acid containing fatty acid material has a PAN rosin acid concentration or content of about 0.5%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 10.5%, about 11%, about 11.5%, about 12%, about 12.5%, about 13%, about 13.5%, about 14%, about 14.5%, about 15%, about 15.5%, about 16%, about 16.5%, about 17%, about 17.5%, about 18%, about 18.5%, about 19%, about 19.5%, about 20%, about 20.5%, about 21%, about 21.5%, about 22%, about 22.5%, about 23%, about 23.5%, about 24%, about 24.5%, about 25%, about 25.5%, about 26%, about 26.5%, about 27%, about 27.5%, about 28%, about 28.5%, about 29%, about 29.5%, about 30%, about 30.5%, about 31%, about 31.5%, about 32%, about 32.5%, about 33%, about 33.5%, about 34%, about 34.5%, about 35%, about 35.5%, about 36%, about 36.5%, about 37%, about 37.5%, about 38%, about 38.5%, about 39%, about 39.5%, about 40%, about 40.5%, about 41%, about 41.5%, about 42%, about 42.5%, about 43%, about 43.5%, about 44%, about 44.5%, about 45%, about 45.5%, about 46%, about 46.5%, about 47%, about 47.5%, about 48%, about 48.5%, about 49%, about 49.5%, or about 50%.

PAN rosin acid concentration/content can be determined by GC. For example, in any aspect or embodiment described herein, the PAN rosin acid concentration/content can be determined according to ASTM D-5974-15 or a modification thereof, which are within the general knowledge of those skilled in the art. For example, the ASTM D-5974-15 method can be modified by using, e.g., a non-polar column (e.g., SPB-5), instead of a polar column, to allow for the use of high temperatures, which allows for substances with higher boiling points to elute out from the column, and/or faster heating rates, which can accelerate the analysis. In any aspect or embodiment described herein, the correction factor for heavies estimation can be determined by the GPC method. PAN rosin acid concentration/content can alternatively be determined by GS-Mass Spectroscopy utilizing the ASTM D-5974-15 method, including modifications that one skilled in the art would appreciate (such as, a non-polar column may be utilized to allow for faster heating rates and higher temperature, which accelerates the analysis).

In any aspect or embodiment described herein, the heavies in the low titer fatty acid material (i.e., the low titer fatty acid material comprising rosin acid) is less than or equal to about 40% (e.g., about 0.5 to about 40%, about 5 to about 40%, about 5 to about 35%, or about 15 to about 28%) of the low titer fatty acid composition. In any aspect or embodiment described herein, the heavies are dimer and trimer fatty or rosin acids that have a higher boiling point than the monomer fatty and rosin acids, which are usually formed during the distillation process. In any aspect or embodiment described herein, the concentration and content of heavies in the low titer fatty acid material can be determined, e.g., by the GPC. For example, in certain embodiments, the low titer fatty acid material (i.e., the low titer rosin acid containing fatty acid material) comprises ≤about 40%, ≤about 35%, ≤about 30%, ≤about 25%, ≤about 20%, ≤about 15%, ≤about 10%, ≤about 5%, about 0.5% to about 40%, about 0.5% to about 35%, about 0.5% to about 30%, about 0.5% to about 25%, about 0.5% to about 20%, about 0.5% to about 15%, about 0.5% to about 10%, about 0.5% to about 5%, about 5% to about 40%, about 5% to about 35%, about 5% to about 30%, about 5% to about 25%, about 5% to about 20%, about 5% to about 15%, about 5% to about 10%, about 10% to about 40%, about 10% to about 35%, about 10% to about 30%, about 10% to about 25%, about 10% to about 20%, about 10% to about 15%, about 15% to about 40%, about 15% to about 35%, about 15% to about 30%, about 15% to about 25%, about 15% to about 20%, about 20% to about 50%, about 20% to about 35%, about 20% to about 30%, about 20% to about 25%, about 25% to about 40%, about 25% to about 35%, about 25% to about 30%, about 30% to about 40%, or about 35% to about 40% heavies from the tall oil distillation process or crude tall oil refining (e.g., dimers, trimmers, or other heavier components).

In any aspect or embodiment described herein, the low titer fatty acid material, low titer fatty acid material comprising rosin acid, or low titer rosin acid containing fatty acid material has a Gardner color index in a range from about 4.0 to about 17.0 (e.g., about 4.0 to about 14.7, about 6.0 to about 14.7, or about 9.0 to about 13.0). For example, in certain embodiments, the low titer fatty acid material has a Gardner color index of about 4.0 to about 17.0, about 4.0 to about 15.0, about 4.0 to about 14.7, about 4.0 to about 13.0, about 4.0 to about 12.0, about 4.0 to about 10.0, about 4.0 to about 8.0, about 4.0 to about 6.0, about 6.0 to about 17.0, about 6.0 to about 15.0, about 6.0 to about 14.7, about 6.0 to about 13.0, about 6.0 to about 12.0, about 6.0 to about 10.0, about 6.0 to about 8.0, about 8.0 to about 17.0, about 8.0 to about 15.0, about 8.0 to about 14.7, about 8.0 to about 13.0, about 8.0 to about 12.0, about 8.0 to about 10.0, about 10.0 to about 17.0, about 10.0 to about 15.0, about 10.0 to about 14.7, about 10.0 to about 13.0, about 10.0 to about 12.0, about 12.0 to about 17.0, about 12.0 to about 15.0, about 12.0 to about 14.0, or about 14.0 to about 17.0. In any aspect or embodiment described herein, the Gardner color index is determined with ASTM D6166-12 (2016).

In any aspect or embodiment described herein, the low titer fatty acid material, low titer fatty acid material comprising rosin acid, or low titer rosin acid containing fatty acid material has a Chemical Abstracts Service Registry (CAS) No. 8002-26-4; a blend or mixture of a tall oil with a CAS No. 8002-26-4 and a TOFA with a CAS No. 61790-12-3; a blend or mixture of CAS No. 8050-09-7 (Resin-95 or rosin R-24) and a TOFA with a CAS No. 61790-12-3; a blend or mixture of CAS No. 8002-26-4, CAS No. 61790-12-3, and CAS No. 8050-09-7; or a dis-proportionated tall oil with a CAS No. 68152-92-1 optionally blended or mixed with another low titer fatty acid material, TOFA, DTO, or tall oil.

Amine Material

In any aspect or embodiment described herein, the amine material includes at least one of diethylenetriamine (DETA), hydroxyethyldiethylenetriamine (HEDETA), 2-piperazinoethanol, triethylenetetramine (TETA), Tetraethylenepentamine mixtures (TEPA), pentaethylene hexamine (PEHA) heptaethyleneoctamine (HEOA), hexaethyleneheptamine (HEHA)amine HST, amine DCT, aminoethylpiperazine (AEP), dimethylaminopropylamine (DMAPA), aminoethylethanolamine (AEEA), diethanolamine (DEA), triethanolamine (TEA), monoethanolamine, other higher ethylene amines or a combination thereof.

In any aspect or embodiment described herein the amine material has an amine value of about 700 to about 1300 mg/g (e.g., about 700 mg/g to about 900 mg/g). For example, in any aspect or embodiment described herein, the amine material has an amine value of about 700 to about 1300 mg/g, about 700 to about 1200 mg/g, about 700 to about 1100 mg/g, about 700 to about 1000 mg/g, about 700 to about 900 mg/g, about 700 to about 875 mg/g, about 700 to about 850 mg/g, about 700 to about 825 mg/g, about 700 to about 800 mg/g, about 700 to about 775 mg/g, about 700 to about 750 mg/g, about 700 to about 725 mg/g, about 725 to about 1300 mg/g, about 725 to about 1200 mg/g, about 725 to about 1100 mg/g, about 725 to about 1000 mg/g, about 725 to about 900 mg/g, about 725 to about 875 mg/g, about 725 to about 850 mg/g, about 725 to about 825 mg/g, about 725 to about 800 mg/g, about 725 to about 775 mg/g, about 725 to about 750 mg/g, about 750 to about 1300 mg/g, about 750 to about 1200 mg/g, about 750 to about 1100 mg/g, about 750 to about 1000 mg/g, about 750 to about 900 mg/g, about 750 to about 875 mg/g, about 750 to about 850 mg/g, about 750 to about 825 mg/g, about 750 to about 800 mg/g, about 750 to about 775 mg/g, about 775 to about 1300 mg/g, about 775 to about 1200 mg/g, about 775 to about 1100 mg/g, about 775 to about 1000 mg/g, about 775 to about 900 mg/g, about 775 to about 875 mg/g, about 775 to about 850 mg/g, about 775 to about 825 mg/g, about 775 to about 800 mg/g, about 800 to about 1300 mg/g, about 800 to about 1200 mg/g, about 800 to about 1100 mg/g, about 800 to about 1000 mg/g, about 800 to about 900 mg/g, about 800 to about 875 mg/g, about 800 to about 850 mg/g, about 800 to about 825 mg/g, about 835 to about 1300 mg/g, about 825 to about 1200 mg/g, about 825 to about 1100 mg/g, about 825 to about 1000 mg/g, about 825 to about 900 mg/g, about 825 to about 875 mg/g, about 825 to about 850 mg/g, about 850 to about 1300 mg/g, about 850 to about 1200 mg/g, about 850 to about 1100 mg/g, about 850 to about 1000 mg/g, about 850 to about 900 mg/g, about 850 to about 875 mg/g, about 875 to about 1300 mg/g, about 875 to about 1200 mg/g, about 875 to about 1100 mg/g, about 875 to about 1000 mg/g, about 875 to about 900 mg/g, about 900 to about 1300 mg/g, about 900 to about 1200 mg/g, about 900 to about 1100 mg/g, about 900 to about 1000 mg/g, about 1000 to about 1300 mg/g, about 1000 to about 1200 mg/g, about 1000 to about 1100 mg/g, about 1100 to about 1300 mg/g, about 1100 to about 1200 mg/g, about 1100 to about 1300 mg/g, about 1100 to about 1200 mg/g, or about 1200 to about 1300 mg/g. In any aspect or embodiment described herein, the amine material has an amine value of about 700, about 701, about 702, about 703, about 704, about 705, about 706, about 707, about 708, about 709, about 710, about 711, about 712, about 713, about 714, about 715, about 716, about 717, about 718, about 719, about 720, about 721, about 722, about 723, about 724, about 725, about 726, about 727, about 728, about 729, about 730, about 731, about 732, about 733, about 734, about 735, about 736, about 737, about 738, about 739, about 740, about 741, about 742, about 743, about 744, about 745, about 746, about 747, about 748, about 749, about 750, about 751, about 752, about 753, about 754, about 755, about 756, about 757, about 758, about 759, about 760, about 761, about 762, about 763, about 764, about 765, about 766, about 767, about 768, about 769, or about 770, about 771, about 772, about 773, about 774, about 775, about 776, about 777, about 778, about 779, about 780, about 781, about 782, about 783, about 784, about 785, about 786, about 787, about 788, about 789, about 790, about 791, about 792, about 793, about 794, about 795, about 796, about 797, about 798, about 799, about 800, about 801, about 802, about 803, about 804, about 805, about 806, about 807, about 808, about 809, about 810, about 811, about 812, about 813, about 814, about 815, about 816, about 817, about 818, about 819, about 820, about 821, about 822, about 823, about 824, about 825, about 826, about 827, about 828, about 829, about 830, about 831, about 832, about 833, about 834, about 835, about 836, about 837, about 838, about 839, about 840, about 841, about 842, about 843, about 844, about 845, about 846, about 847, about 848, about 849, about 850, about 851, about 852, about 853, about 854, about 855, about 856, about 857, about 858, about 859, about 860, about 861, about 862, about 863, about 864, about 865, about 867, about 868, about 869, about 870, about 871, about 872, about 873, about 874, about 875, about 876, about 877, about 878, about 879, about 880, about 881, about 882, about 883, about 884, about 885, about 886, about 887, about 888, about 889, about 890, about 891, about 892, about 893, about 894, about 895, about 896, about 897, about 898, about 899, about 900 mg/g, about 901, about 902, about 903, about 904, about 905, about 906, about 907, about 908, about 909, about 910, about 911, about 912, about 913, about 914, about 915, about 916, about 917, about 918, about 919, about 920, about 921, about 922, about 923, about 924, about 925, about 926, about 927, about 928, about 929, about 930, about 931, about 932, about 933, about 934, about 935, about 936, about 937, about 938, about 939, about 940, about 941, about 942, about 943, about 944, about 945, about 946, about 947, about 948, about 949, about 950, about 951, about 952, about 953, about 954, about 955, about 956, about 957, about 958, about 959, about 960, about 961, about 962, about 963, about 964, about 965, about 967, about 968, about 969, about 970, about 971, about 972, about 973, about 974, about 975, about 976, about 977, about 978, about 979, about 980, about 981, about 982, about 983, about 984, about 985, about 986, about 987, about 988, about 989, about 990, about 991, about 992, about 993, about 994, about 995, about 996, about 997, about 998, about 999, about 1000, about 1001, about 1002, about 1003, about 1004, about 1005, about 1006, about 1007, about 1008, about 1009, about 1010, about 1011, about 1012, about 1013, about 1014, about 1015, about 1016, about 1017, about 1018, about 1019, about 1020, about 1021, about 1022, about 1023, about 1024, about 1025, about 1026, about 1027, about 1028, about 1029, about 1030, about 1031, about 1032, about 1033, about 1034, about 1035, about 1036, about 1037, about 1038, about 1039, about 1040, about 1041, about 1042, about 1043, about 1044, about 1045, about 1046, about 1047, about 1048, about 1049, about 1050, about 1051, about 1052, about 1053, about 1054, about 1055, about 1056, about 1057, about 1058, about 1059, about 1060, about 1061, about 1062, about 1063, about 1064, about 1065, about 1067, about 1068, about 1069, about 1070, about 1071, about 1072, about 1073, about 1074, about 1075, about 1076, about 1077, about 1078, about 1079, about 1080, about 1081, about 1082, about 1083, about 1084, about 1085, about 1086, about 1087, about 1088, about 1089, about 1090, about 1091, about 1092, about 1093, about 1094, about 1095, about 1096, about 1097, about 1098, about 1099, about 1100, about 1101, about 1102, about 1103, about 1104, about 1105, about 1106, about 1107, about 1108, about 1109, about 1110, about 1111, about 1112, about 1113, about 1114, about 1115, about 1116, about 1117, about 1118, about 1119, about 1121, about 1121, about 1122, about 1123, about 1124, about 1125, about 1126, about 1127, about 1128, about 1129, about 1131, about 1131, about 1132, about 1133, about 1134, about 1135, about 1136, about 1137, about 1138, about 1139, about 1141, about 1141, about 1142, about 1143, about 1144, about 1145, about 1146, about 1147, about 1148, about 1149, about 1151, about 1151, about 1152, about 1153, about 1154, about 1155, about 1156, about 1157, about 1158, about 1159, about 1161, about 1161, about 1162, about 1163, about 1164, about 1165, about 1167, about 1168, about 1169, about 1171, about 1171, about 1172, about 1173, about 1174, about 1175, about 1176, about 1177, about 1178, about 1179, about 1181, about 1181, about 1182, about 1183, about 1184, about 1185, about 1186, about 1187, about 1188, about 1189, about 1191, about 1191, about 1192, about 1193, about 1194, about 1195, about 1196, about 1197, about 1198, about 1199, about 1200, about 1201, about 1202, about 1203, about 1204, about 1205, about 1206, about 1207, about 1208, about 1209, about 1210, about 1211, about 1212, about 1213, about 1214, about 1215, about 1216, about 1217, about 1218, about 1219, about 1221, about 1221, about 1222, about 1223, about 1224, about 1225, about 1226, about 1227, about 1228, about 1229, about 1231, about 1231, about 1232, about 1233, about 1234, about 1235, about 1236, about 1237, about 1238, about 1239, about 1241, about 1241, about 1242, about 1243, about 1244, about 1245, about 1246, about 1247, about 1248, about 1249, about 1251, about 1251, about 1252, about 1253, about 1254, about 1255, about 1256, about 1257, about 1258, about 1259, about 1261, about 1261, about 1262, about 1263, about 1264, about 1265, about 1267, about 1268, about 1269, about 1271, about 1271, about 1272, about 1273, about 1274, about 1275, about 1276, about 1277, about 1278, about 1279, about 1281, about 1281, about 1282, about 1283, about 1284, about 1285, about 1286, about 1287, about 1288, about 1289, about 1291, about 1291, about 1292, about 1293, about 1294, about 1295, about 1296, about 1297, about 1298, about 1299, or about 1300 mg/g.

In any aspect or embodiment described herein, amine value can be determined through titration. For example, in any aspect or embodiment described herein, amine value can be determined by titration with 0.5N HCl. An exemplary method that may be used to determine amine value through titration is described below in the Examples.

In any aspect or embodiments described herein, the amine material is or includes the chemical composition having Chemical Abstracts Service (CAS) Registry No. 68910-05-4. This composition is the distillation residuum bottoms composition remaining from the process wherein monoethanolamine (i.e., 2-aminoethanol) is reacted with ammonia to produce a reaction product which is then fractionated to recover a piperazine distillate product therefrom, thus leaving the remaining CAS Reg. No. 68910-05-4 distillation residuum bottoms composition. The distillation residuum bottoms composition CAS Reg. No. 68910-05-4 is commercially available, for example, from Dow® Chemical Co. (Marlborough, Mass.) under the name AMINE HST and is also available from BASF under the name AMIX 1000 or Berolamine 20 (BA-20). AMINE HST has: an estimated boiling point (760 mmHg) of 256° C., an estimated flashpoint (closed cup) of 146° C., an estimated vapor pressure of less than 0.01 mmHg at 20° C., an estimated vapor density (air=1) of 4.6, an estimated specific gravity (water=1) of 1.0-1.3 at 20° C./20° C., an estimated solubility in water of 100% by weight at 20° C., and an estimated pour point of −24° C.

Thus, in any aspect or embodiment described herein, the amine material is or includes a chemical composition having CAS Registry No. 68910-05-4, such as at least one of: AMINE HST (e.g., an amine material having at least one of: an estimated boiling point (760 mmHg) of 256° C., an estimated flashpoint (closed cup) of 146° C., an estimated vapor pressure of less than 0.01 mmHg at 20° C., an estimated vapor density (air=1) of 4.6, an estimated specific gravity (water=1) of 1.0-1.3 at 20° C./20° C., an estimated solubility in water of 100% by weight at 20° C., an estimated pour point of −24° C., or a combination thereof), BA-20 (e.g., an amine material having at least one of: an amine value of at least 1100 mg/g, a viscosity at 50° C. that is equal to or less than 100, a melting or freezing point of at 1013 hPa that is less than −30° C., a boiling point at 1013 hPa of about 254° C., a flash point at 1013 hPa of about 176° C., a viscosity (such as a dynamic viscosity) at 50° C. of about 40 mPa·s, an auto-ignition temperature at 1013 hPa of about 355° C., a relative density at 20° C. of about 1024, about 45% alkanolamines (e.g., AEEA, DEA, hydroxymethyl DETA, and higher order alkanolamines), a vapor pressure at 20° C. of about 0.00009 hPa, about 55% higher polyethylene polyamines (e.g., isomers of TETA, TEPA, PEHA, and higher order polyethylene polyamines), or AMIX 1000 (e.g., an amine material having at least one of: an amine value of about 1000 mg/g, a melting temperature of about −30° C., a boiling temperature of about 236° C. to about 310° C., a density at 20° C. of about 1.04 g/cm$^3$, a flash point of about 132° C., an ignition temperature of about 360° C., or a combination thereof).

Method of Making the LGS Tolerant Emulsifier

The present disclosure also provides methods of making a LGS tolerant emulsifier (i.e., a MDTA emulsifier or a LGS tolerant MDTA emulsifier), the method comprising: reacting the low titer fatty acid material an amine material to produce an amido-amine reaction product; and reacting the amido-amine reaction product with maleic anhydride to produce a maleated amido-amine reaction product.

In any aspect or embodiment described herein, the method of making a LGS tolerant MDTA emulsifier comprising reacting a low titer fatty acid material and an amine material at room temperature and then elevated temperatures to produce an amido-amine reaction product; and reacting the amido-amine reaction product with maleic anhydride at elevated temperature to produce a maleated-amido-amine reaction product. In any aspect or embodiment described herein, the method of making a LGS tolerant MDTA emulsifier comprising reacting a low titer fatty acid material and an amine material at room temperature first, followed by heating to about 110 to about 150° C. (e.g., from about 130 to about 140° C.), followed by heating to about 175 to about 250° C. (e.g., from about 200 to about 225° C.), to produce an amido-amine reaction product; and reacting the amido-amine reaction product with maleic anhydride at about 60 to about 90°, and optionally hold for up to about 1 hour (e.g., about 30 minutes), to produce a maleated amido-amine reaction product. In certain embodiments, the fatty acid material and amine material are incubated at the elevated temperature for up to about 4 hours (e.g., about 3 hours, about 2 hours, about 1 hour, about 1 to about 4 hours, about 1 to about 3 hours, about 1 to about 2 hours, about 2 to about 4 hours, about 2 to about 3 hours, or about 3 hours to about 4 hours).

Invert Emulsion Fluid

Another aspect of the present disclosure provides an invert emulsion fluid (IEF) comprising the emulsifier of the present disclosure and at least one of: a non-aqueous continuous phase, a discontinuous hygroscopic phase like brine, an additive, or a combination thereof. In any aspect or embodiment described herein, the additive includes at least one of (e.g., 1, 2, 3, 4, 5, or 6, or more) a rheology modifier, emulsifier, wetting agents, viscosifiers, lime, salts, fluid loss additives, lost circulation materials, weighting agents, or a combination thereof. The IEF of the present disclosure demonstrated the surprising and unexpected ability to control (i.e., reduced) rheology even in the presence of relatively high concentrations of LGS as compared to a maleated TOFA amine emulsifier, which is generally recognized as the industry standard, as disclosed in, e.g., U.S. Pat. No. 8,927,468 B2, which is incorporated herein by reference in its entirety, including a non-spray dried version of the emulsifier (see e.g., page 4 of U.S. Pat. No. 8,927,468 B2).

In any aspect or embodiment described herein, the IEF comprises a high volume, amount, or concentration of LGS. For example, the inverted emulsion fluid can comprise from about 4% to about 12% V/V of low gravity solids. For example, in any aspect or embodiment described herein, the IEF comprises about 4% to about 12%, about 4% to about 10%, about 4% to about 8%, about 4% to about 6%, about 6% to about 12%, about 6% to about 10%, about 6% to about 8%, about 8% to about 12%, about 8% to about 10%, or about 10% to about 12% V/V of low gravity solids. In any aspect or embodiment described herein, the IEF comprises about 4%, about 4.5%, about 5%, about 5.5%, about 6%, about 6.5%, about 7%, about 7.5%, about 8%, about 8.5%, about 9%, about 9.5%, about 10%, about 10.5%, about 11%, about 11.5%, or about 12% V/V of low gravity solids.

In any aspect or embodiment described herein, the LGS have a specific gravity of about 2.0 to about 3.0. For example, in certain embodiments, the LGS has a specific gravity of about 2.0 to about 3.0, about 2.0 to about 2.9, about 2.0 to about 2.8, about 2.0 to about 2.7, about 2.0 to about 2.6, about 2.0 to about 2.5, about 2.0 to about 2.4, about 2.0 to about 2.3, about 2.0 to about 2.2, about 2.0 to about 2.1, about 2.1 to about 3.0, about 2.1 to about 2.9, about 2.1 to about 2.8, about 2.1 to about 2.7, about 2.1 to about 2.6, about 2.1 to about 2.5, about 2.1 to about 2.4, about 2.1 to about 2.3, about 2.1 to about 2.2, about 2.2 to about 3.0, about 2.2 to about 2.9, about 2.2 to about 2.8, about 2.2 to about 2.7, about 2.2 to about 2.6, about 2.2 to about 2.5, about 2.2 to about 2.4, about 2.2 to about 2.3, about 2.3 to about 3.0, about 2.3 to about 2.9, about 2.3 to about 2.8, about 2.3 to about 2.7, about 2.3 to about 2.6, about 2.3 to about 2.5, about 2.3 to about 2.4, about 2.4 to about 3.0, about 2.4 to about 2.9, about 2.4 to about 2.8, about 2.4 to about 2.7, about 2.4 to about 2.6, about 2.4 to about 2.5, about 2.5 to about 3.0, about 2.5 to about 2.9, about 2.5 to about 2.8, about 2.5 to about 2.7, about 2.5 to about 2.6, about 2.6 to about 3.0, about 2.6 to about 2.9, about 2.6 to about 2.8, about 2.6 to about 2.7, about 2.7 to about 3.0, about 2.7 to about 2.9, about 2.7 to about 2.8, about 2.8 to about 3.0, about 2.8 to about 2.9, or about 2.9 to about 30. In certain embodiments, the LGS has a specific gravity of about 2.0, 2.1, 2.2, 2.3, 2.4, 2.5, 2.6, 2.7, 2.8, 2.9, or 3.0.

In any aspect or embodiment described herein, the low gravity solids are argillaceous solids. In any aspect or embodiment described herein, the LGS are drill solids. In any aspect or embodiment described herein, the LGS is or includes calcium montmorillonite. For example, the LGS can be REV DUST® (MILWHITE, INC., Brownsville, TV).

In any aspect or embodiment described herein, the IEF of the present disclosure has a low fluid loss, e.g. a fluid loss of no greater than (i.e., less than or equal to) about 20 mL at 350° F. in about 30 minutes. Thus, the IEF of the present disclosure does not compromise on fluid loss performance and has sufficient emulsion stability for a workable fluid.

In any aspect or embodiment described herein, the IEF of the present disclosure has a low HTHP fluid loss, e.g., a fluid loss between about 1 and about 20 mL at 350° F. in about 30 minutes. See, e.g., API Recommended Practice 13B-2, Fourth Edition, Recommended Practice for Field Testing of Oil-based Drilling Fluids, for the test method to conduct the HTHP filtration test, i.e., at the test temperature indicated. Thus, the IEF of the present disclosure do not compromise on their fluid loss performance and have sufficient emulsion stability for a workable fluid. For example, in any aspect or embodiment described herein, the fluid loss of the IEF of the present disclosure is about 1 mL to about 20 mL, about 1 mL to about 15 mL, about 1 mL to about 10 mL, about 1 mL to about 5 mL, about 5 mL to about 20 mL, about 5 mL to about 15 mL, about 5 mL to about 10 mL, about 10 mL to about 20 mL, about 10 mL to about 15 mL, or about 15 mL to about 20 mL.

In any aspect or embodiment described herein, the IEF of the present disclosure has a lower rheology than a similarly formulated IEF comprising a maleated TOFA amine emulsifier. In an embodiment, the IEF of the present disclosure has a rheology that is lower than a similarly formulated IEF comprising a maleated TOFA amine emulsifier as determined by a decrease in Fann 35 rheometer readings from 600 rotations per minute (rpm) to 3 rpm, e.g., at 150° F. In certain embodiments, the IEF of the present disclosure has a rheology that is about 10-about 92% (e.g., about 10 to about 92% or about 50 to about 92%) lower than a similarly formulated IEF comprising a maleated TOFA amine emulsifier as determined by Fann 35 rheometer readings from 600 rpm to 3 rpm at 150° F. For example, in any aspect or embodiment described herein, the IEF of the present disclosure has a rheology, as determined by Fann 35 rheometer readings from 600 rpm to 3 rpm at 150° F., that is about 10 to about 92%, about 10 to about 95%, about 10 to about 80%, about 10 to about 70%, about 10 to about 60%, about 10 to about 50%, about 10 to about 40%, about 10 to about 30%, about 20 to about 92%, about 20 to about 85%, about 20 to about 80%, about 20 to about 70%, about 20 to about 60%, about 20 to about 50%, about 20 to about 40%, about 30 to about 92%, about 30 to about 85%, about 30 to about 80%, about 30 to about 70%, about 30 to about 60%, about 30 to about 50%, about 40 to about 92%, about 40 to about 85%, about 40 to about 80%, about 40 to about 70%, about 40 to about 60%, about 50 to about 92%, about 50 to about 85%, about 50 to about 80%, about 50 to about 70%, about 60 to about 92%, 60 to about 85%, about 60 to about 80%, or about 70 to about 92% lower than a similarly formulated IEF comprising a maleated TOFA amine emulsifier. In any of the aspects or embodiments described herein, the rheology of the IEF is determined at 100 ppb REVDUST tested under standard conditions. In any aspect or embodiment described herein, HPHT fluid loss and rheology are determined using the methods/conditions described in API Recommended Practice 13B-2, Fourth Edition, Recommended Practice for Field Testing of Oil-based Drilling Fluids). It should be noted that similar decreases are expected when rheology is measured at different temperatures, such as 120° F.

In any aspect or embodiment described herein, the IEF of the present disclosure has a lower gel strength than a similarly formulated IEF with a maleated TOFA amine emulsifier. In certain embodiments, the IEF of the present disclosure has a gel strength that is about 10 to about 92% (e.g., about 25 to about 85% or about 50 to about 85%) lower than a similarly formulated IEF comprising a maleated TOFA amine emulsifier at 150° F. For example, in any aspect or embodiment described herein, the IEF of the present disclosure has a gel strength at 150° F. that is about 10 to about 92%, about 10 to about 95%, about 10 to about 80%, about 10 to about 70%, about 10 to about 60%, about 10 to about 50%, about 10 to about 40%, about 10 to about 30%, about 20 to about 92%, about 20 to about 85%, about 20 to about 80%, about 20 to about 70%, about 20 to about 60%, about 20 to about 50%, about 20 to about 40%, about 30 to about 92%, about 30 to about 85%, about 30 to about 80%, about 30 to about 70%, about 30 to about 60%, about 30 to about 50%, about 40 to about 92%, about 40 to about 85%, about 40 to about 80%, about 40 to about 70%, about 40 to about 60%, about 50 to about 92%, about 50 to about 85%, about 50 to about 80%, about 50 to about 70%, about 60 to about 92%, 60 to about 85%, about 60 to about 80%, or about 70 to about 92% lower than a similarly formulated IEF comprising a maleated TOFA amine emulsifier. It should be noted that one of ordinary skill in the art would expect similar decreases in fluid gel strength when rheology is measured at a different temperature, such as 120° F.

In any aspect or embodiment described herein, the IEF of the present disclosure has a lower yield stress (Tau0) than a similarly formulated IEF with a maleated TOFA amine emulsifier. In certain embodiments, the IEF of the present disclosure has a yield stress that is about 10 to about 92% lower than a similarly formulated IEF comprising a maleated TOFA amine emulsifier at 150° F. This decrease is even observed in presence of a high volume of low gravity solids as described herein (e.g. greater than about 10% V/V). For example, in any aspect or embodiment described herein, the IEF of the present disclosure has a yield stress at 150° F. that is about 10 to about 92%, about 10 to about 85%, about 10 to about 80%, about 10 to about 70%, about 10 to about 60%, about 10 to about 50%, about 10 to about 40%, about 10 to about 30%, about 20 to about 92%, about 20 to about 85%, about 20 to about 80%, about 20 to about 70%, about 20 to about 60%, about 20 to about 50%, about 20 to about 40%, about 30 to about 92%, about 30 to about 85%, about 30 to about 80%, about 30 to about 70%, about 30 to about 60%, about 30 to about 50%, about 40 to about 92%, about 40 to about 85%, about 40 to about 80%, about 40 to about 70%, about 40 to about 60%, about 50 to about 92%, about 50 to about 85%, about 50 to about 80%, about 50 to about 70%, about 60 to about 92%, 60 to about 85%, about 60 to about 80%, or about 70 to about 92% lower than a similarly formulated IEF comprising a maleated TOFA amine emulsifier. It should be noted that similar decreases in yield stress is expected when rheology is measured at a different temperature, such as 120° F. In any aspect or embodiment described herein, the IEF of the present disclosure has a gel strength of about 10 to about 30 (e.g., about 10 to about 20, about 20 to about 30, or about 15 to about 25).

In any aspect or embodiment described herein, the IEF of the present disclosure is used for gas drilling, oil drilling, or both.

Drilling Fluid

Another aspect of the present disclosure provides a drilling fluid that comprises the IEF of the present disclosure, the LGS tolerant emulsifier of the present disclosure, or both.

In another aspect or embodiment described herein, the drilling fluid of the present disclosure has a lower gel strength than a similarly formulated drilling fluid comprising a maleated TOFA amine emulsifier, even in presence of a high volume or concentration of LGS (e.g. from about 4% to about 12% V/V of the drilling fluid).

In any aspect or embodiment described herein, the drilling fluid of the present disclosure has a lower rheology than a similarly formulated drilling fluid comprising a maleated TOFA amine emulsifier, even in presence of a high volume or concentration of LGS (e.g. from about 4% to about 12% V/V of the drilling fluid).

In any aspect or embodiment described herein, the drilling fluid is used for gas or oil drilling.

Method of Drilling a Well

A further aspect of the disclosure provides a method of drilling a well. The method comprises drilling a well bore and circulating the drilling fluid of the any aspect or embodiment described herein through said well bore when drilling the well bore.

Examples

The embodiments described above in addition to other embodiments can be further understood regarding the following examples.

Rosin Acid (RA) Determination.

RA concentration was determined by titration. A modified Glidden procedure was utilized for RA concentration of about 15% or less, and a modified Wolff Method was utilized for RA concentration of about 15% or greater. In particular, under the modified Wolff Method, 4.5-5.5 grams of the low titer fatty acid material, 90-110 mL of methanol, and 5 mL of methyl sulfuric acid (20% in methanol) was added to an Erlenmeyer flask, and under the modified Glidden Method, 39-41 grams of the low titer fatty acid material, 140-160 mL of methanol, and 10 mL of methyl sulfuric acid (20% in methanol) was added to an Erlenmeyer flask. If the solution prepared under the modified or Wolff Method or the modified Glidden method is cloudy, toluene is added (up to 30 mL) until the solution is clear. The flask of clear solution was connected to a condenser and refluxed for 20 minutes on a hotplate. The solution was then cooled. The rosin acid number was then determined through titration of the cooled solution with 0.5N KOH in methanol on a 888 Titrando Autotitrator (Metrohm, Riverview, Fla.).

Acid Number and Amine Value Determination.

Two grams of the low titer fatty acid material or amine material was added to a beaker. The low titer fatty acid material was dissolved in methanol or a mixture of methanol and Toluene or isopropanol using agitation and/or heat, as required for complete dissolution. The amine material was dissolved in 75 mL of isopropanol, using agitation and/or heat, as required for complete dissolution. Acid number was determined via titration with 0.5N KOH in methanol and the amine value was determined via titration with 0.5 HCL in methanol on a 888 Titrando Autotitrator (Metrohm, Riverview, Fla.).

Titer Point Determination.

Titer point of the low titer fatty acid material was determined via ASTM D1982-61. Briefly, the low titer fatty acid material was added to a test tube. A Thermometer and stirring wire was added to the test tube. The test tube assembly was placed in a frozen cold bath assembly. The stir wire completed approximately one-hundred 1-2" up-and-down motions per minute. The temperature of the low titer fatty acid material was read every 15 seconds until the temperature remained constant for 30 seconds or until a rise in temperature was observed. Stirring was discontinued and any temperature rise was noted (exotherm portion). The titer point is the highest temperature observed during the exotherm portion before the temperature began to decrease.

Gardner Color Index Determination.

The Gardner color index was determined according to ASTM D6166-12 (2016).

Amount of Fatty Acid and Rosin Acid Determination.

The amount of fatty acid and rosin acid in the low titer fatty acid material or components thereof was determined utilized the method described in ASTM D5974-15.

Preparation of an Exemplary Emulsifier of the Present Disclosure: C2-B® Based Emulsifier (i.e., a Maleated Amido Amine Based on C2-B®).

C2-B® was utilized as the low titer fatty acid material and is a low titer fatty acid material collected as the bottoms product during the production of low rosin (<5%) and low Gardner Color index (<7.0) tall oil fatty acid (TOFA) from refinery columns during the distillation of crude tall oil (CTO). The acid number of the C2-B® can vary from about 143-about 185 mg/g, but typically is about 155-about 174 mg/g. Amine HST (CAS #68910-05-4) was used as the amine material and is available as an amine stream procured from Dow Chemicals, the batch used had an amine value of approximately 750 mg/g.

Preparation of the maleated amido-amine reaction product:
1. About 350 grams (70% w/w) of the C2-B® (preheated) with an acid number of 167.2 mg/gm was added into to the five neck round bottom flask (1000 ml). Under stirring at 90 rpm, 150 grams (30% w/w) of Amine HST was added, which gives an exotherm.
2. Once the temperature was stabilized, the reaction mixture was heated to 135° C. over 35 minutes and then held at 135° C. for 1 hour.
3. The reaction mixture was ramped to 200° C. over 56 minutes and held at 200° C. temperature for 2 hours.
4. After 2 hours, the reaction mixture was cooled to 100° C. The amino-amine reaction product was transferred to a sample bottle. The amine value of this C2-B® based amido-amine (i.e., the amido-amine reaction product) was determined to be 133.9 mg/gm.
5. About 35.78 grams of the amido-amine reaction product was heated to 65° C. in an aluminum can and 19.8 grams of a mineral oil LVT 200 was added.
6. This reaction mixture was stirred while the temperature was maintained at 65° C.
7. During stirring, 4.42 grams of molten Maleic Anhydride (MA) was added dropwise. Since MA addition resulted in an exotherm, the MA addition was controlled to ensure the temperature was maintained at 85° C.
8. After the addition of all the MA, the reaction mixture was stirred, while being held at 85° C., for 1 hour. The reaction mixture was then cool to room temperature.
9. The resulting maleated C2-B amido-amine (i.e. the maleated amido-amine reaction product) had an amine value of 30.29 mg/gm and acid number of 52.59 mg/gm. This samples is labelled as 9160-57-11. Additional exemplary emulsifiers were prepared utilizing similar methods and will now be described in greater detail.

Exemplary and Comparative Emulsifiers utilized in the Examples are shown in Table 1. The Exemplary Emulsifiers (i.e., LGS tolerant emulsifier or MDTA emulsifier) of the disclosure were made with the indicated pure low titer distilled tall oil streams as the low titer fatty acid material and are designated 9139-70-11 (C2-B®), 9160-57-11 (C2-B®), 9177-32-11 (C2-B®), 9177-34-11 (C2-B®), 8998-75B-7 (Altapyne™ M28B) and 8998-75C-7 (Altapyne™ 1430) in Table 1. The Exemplary Emulsifiers made with low titer distilled tall oil streams having acid numbers ranging from 147.9 mg/g to 188.4 mg/g. Commercially available maleated TOFA amido-amine emulsifiers, which are the industry standard, were utilized as Comparative Emulsifiers. The emulsifiers were tested at an effective concentration of 10.7 ppb in the IEF. The formulations of the compositions and reaction conditions are shown in Table 2.

The components of the fluids were mixed, then hot rolled for 16 hours at 325° F. The fluids were then remixed on a multimixer for 5 minutes. Rheology and electrical stability (ES) were examined at 150° F. Fluid loss of the fluids was examined at 350° F., 500 psi differentials.

The rheology data of the invert emulsion fluids was measured at 150° F. and were modeled with the Herschel Buckley (HB) model. The HB model parameters—Tau0 (yield stress), K (consistency index), & n (flow index)—along with the Gel strength at 10 minutes, the Electrical Stability (ES), Fluid loss and Fann 35 rheometer readings from 600 to 3 rpm dial readings are presented in Table 3 and 4 below. All fluids tested were stable after the hot roll (as observed from their texture and appropriate ES values), gave controlled fluid loss values at 350° F., and showed water in the filtrate.

The Gel Strengths with the maleated TOFA amido-amine emulsifiers were very high at 58 units and 74 units. In comparison, the Gel strengths of the Exemplary Emulsifiers made with the low titer fatty acid material of varying acid numbers ranged from 15 to 21 units and 30-31 units. The Maleated TOFA amido-amine-1, 9139-70-11, 9160-57-11, 9177-32-11, and 9177-34-11 were analyzed with a different batch of REV DUST® than the Maleated TOFA amido-amine-2, 8998-75B-7, and 8998-75C-7. Thus, while 8998-75B-7 and 8998-75C-7 have higher Gel strengths than the other Exemplary Emulsifiers, this appears to be a result of the REV DUST batch utilized as the Maleated TOFA amido-amine-2, which is the same product as the Maleated TOFA amido-amine-1, demonstrated a higher Gel strength. Thus, a decrease in Gel strength was observed in each of the Exemplary Emulsifiers as compared to the concomitantly analyzed comparative example.

Similarly, the Tau0 (yield stress) from the HB model were in the range of 5-10 for the Exemplary Emulsifier made with low titer fatty acid material. The commercial available maleated TOFA amine emulsifier demonstrated a very high Tau0 at 39.7 and 59.3.

The appreciable gels are required for suspension whereas the low rheology will help to maintain low ECD (in this case in the presence of high LGS @ 100 ppb).

Figure 2:
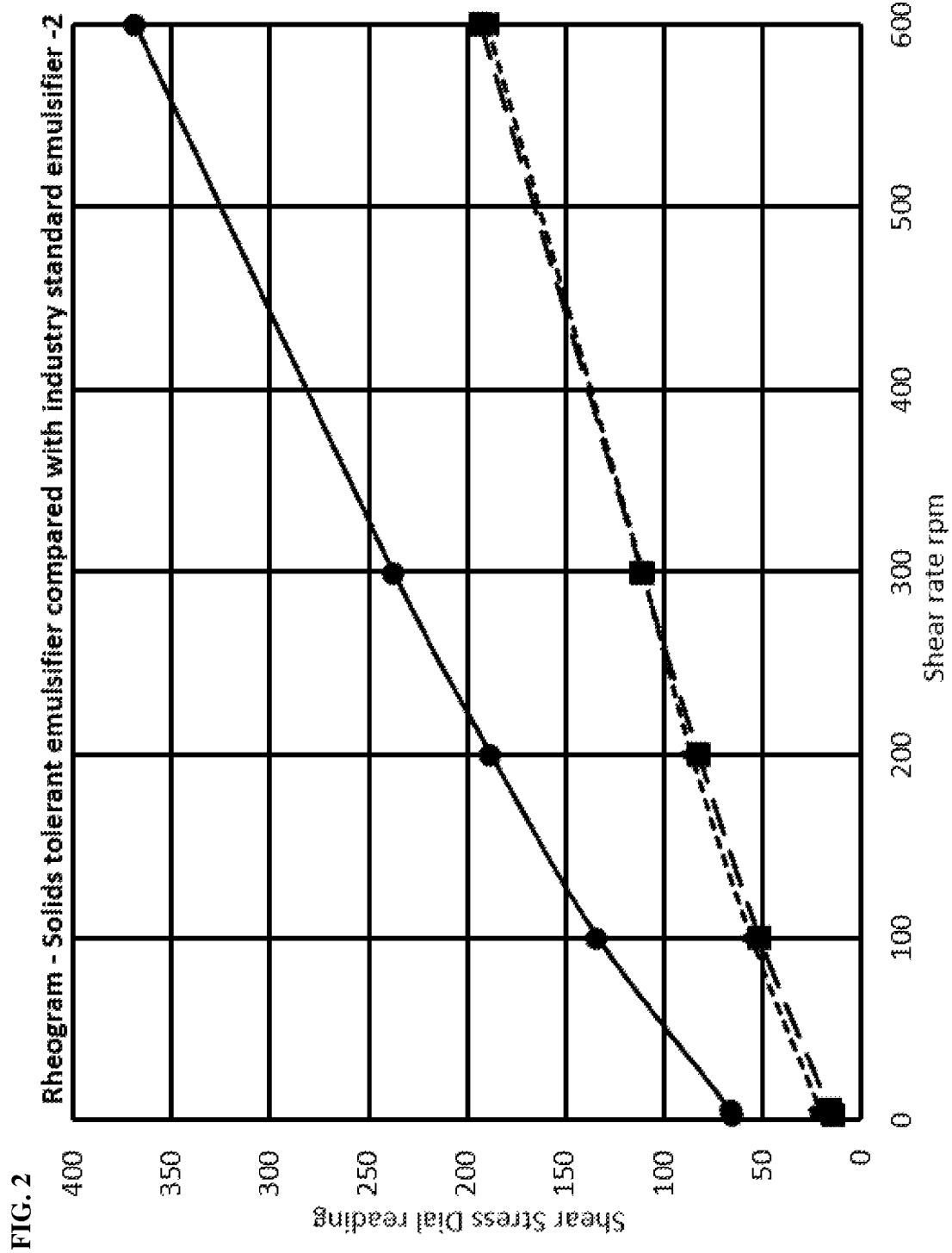
FIG. 2 is a graph illustrating shear stress relative to shear rate of exemplary solids tolerant emulsifiers and a second maleated TOFA amido-amine emulsifier.

FIGS. 1 and 2 present the rheology data of shear stress versus shear rate for exemplary fluids of the present disclosure, as well as comparative fluids. The rheograms of FIGS. 1 and 2 demonstrate that the fluids of the present disclosure formulated with the emulsifier of the present disclosure has low rheology, as compared to the commercially available maleated TOFA amine emulsifier. Thus, the fluids of the present disclosure comprising the emulsifier of the present disclosure were surprisingly able to tolerate the presence of 100 ppb LGS.

A low rheology typically delivers a low ECD, while drilling oil and gas wells. A low ECD generally leads to lower induced fluid losses to the formation. Since invert emulsion fluids are expensive, lower induced fluid losses to the formation are desired. A high concentration of low gravity solids (drilled solids) in the fluid typically increases the overall rheology of the fluid thereby leading to higher ECD, and therefore, higher induced fluid losses to the formation. A low rheology should be coupled with appreciable gels, since when drilling stops and fluid is in a static condition, the gels help to maintain the barite and drilled solids in suspension. A fluid with low gels can lead to barite sag and poor hole cleaning, both of which can lead to loss of precious time at the rig when drilling oil and gas wells.

TABLE 1

Emulsifiers used to test against low gravity solids tolerance in the IEF

| Emulsifier | % Active | AN of low titer fatty acid material (mg/g) | Bisamide Product LTFAM %* | Bisamide Product AMINE HST % | MA % in 100% active Emulsifier** (undiluted) | Hold Temp of Amide Reaction |
|---|---|---|---|---|---|---|
| Maleated TOFA amido-amine - 1 | 66.7 | | | | | |
| 9139-70-11 | 66.7 | 163.0 | 70 | 30 | 11 | 200 |
| 9160-57-11 | 66.7 | 167.2 | 70 | 30 | 11 | 200 |
| 9177-32-11 | 66.7 | 157.8 | 70 | 30 | 11 | 200 |
| 9177-34-11 | 66.7 | 147.9 | 70 | 30 | 11 | 200 |
| 8998-75B-7 | 66.7 | 188.4 | 70 | 30 | 7 | 200 |
| 8998-75C-7 | 66.7 | 181.4 | 70 | 30 | 7 | 200 |
| Maleated TOFA amido-amine - 2 | 66.7 | | | | | |

*LTFAM—low titer fatty acid material.
**MA—maleic anhydride

TABLE 2

Inverted Emulsion Fluid with 100 ppb REV DUST ® formulation

Mix the additives for the given time.
Hot roll at 325° F. for 16 hours
After hot roll, remix on multimixer 5 minutes.
Check rheology and ES at 150° F.
Determine HTHP FL at 350° F., 500 psi differentials

| Mud | S.G | Volume (ml) | Weight (grams) | Time (minutes) |
|---|---|---|---|---|
| ESCAID 110 mineral oil | 0.80 | 156.45 | 125.16 | |
| Emulsifier | 0.96 | 16.67 | 16.00 | 1.0 |
| Lime - Alkalinity Control agent | 2.24 | 1.34 | 3.00 | 1.0 |
| Polymer fluid loss additive based on styrene methacrylate copolymer | 1.03 | 2.91 | 3.00 | 10.0 |
| Brine with CaCl$_2$ (300K WPS) | 1.29 | 67.05 | 86.16 | 10.0 |
| Dimer fatty acid viscosifier | 0.96 | 3.13 | 3.00 | 5.0 |
| REV DUST ® simulate drilled low gravity solids | 2.70 | 37.04 | 100.00 | 5.0 |
| Barite, weighting agent | 4.20 | 65.42 | 274.77 | 10.0 |
| Total weight in grams | | | 611.1 | |
| Total volume in ml | | | 350.0 | |
| Mud weight in ppg | | | 14.57 | |

TABLE 3

Fluid loss, Herschel Buckley parameters, Gel Strength and Electrical Stability of invert emulsion fluids

| Emulsifier | Effective | Gel 10 min @ 150° F. | ES in mV @ 15° F. | Tau0 @ 150° F. | K @ 1500° F. | N @ 150° F. | Fluid loss @ 350° F. |
|---|---|---|---|---|---|---|---|
| Maleated TOFA amido-amine (AN = 192 mg/g) | 10.7 | 58 | 277 | 39.7 | 1.181 | 0.842 | 7.2 (2.4) |
| 9139-70-11 (LTFAM* AN = 163 mg/g) | 10.7 | 21 | 144 | 9.3 | 0.723 | 0.837 | 11.6 (DNM) |
| 9160-57-11 (LTFAM* AN = 167.2 mg/g) | 10.7 | 18 | 144 | 8.0 | 0.477 | 0.888 | 10.0 (3.6) |
| 9177-32-11 (LTFAM* AN = 157.8 mg/g) | 10.7 | 18 | 147 | 6.7 | 0.572 | 0.871 | 8.8 (2.4) |
| 9177-34-11 (LTFAM* AN = 147.9 mg/g) | 10.7 | 15 | 141 | 5.7 | 0.490 | 0.895 | 8.0 (2.0) |
| 8998-75B-7 (LTFAM* AN = 188.35 mg/g) | 10.7 | 30 | 270 | 17.9 | 0.722 | 0.855 | 7.2 |
| 8998-75C-7 (LTFAM* AN = 181.39 mg/g) | 10.7 | 31 | 177 | 12.1 | 0.727 | 0.862 | 7.2 |

TABLE 3-continued

Fluid loss, Herschel Buckley parameters, Gel Strength and Electrical Stability of invert emulsion fluids

| Emulsifier | Effective | Gel 10 min @ 150° F. | ES in mV @ 15° F. | Tau0 @ 150° F. | K @ 1500° F. | N @ 150° F. | Fluid loss @ 350° F. |
|---|---|---|---|---|---|---|---|
| Maleated TOFA amido-amine - 2 (AN = 192 mg/g) | 10.7 | 74 | 300 | 59.3 | 1.859 | 0.800 | 4.0 |

*LTFAM—low titer fatty acid material

TABLE 4

Rheology of inverted emulsion fluids at 600 rpm to 3 rpm dial readings

| | | Rotations per minute at 150° F. | | | | | |
|---|---|---|---|---|---|---|---|
| Emulsifier | Effective concentration | 600 rpm | 300 rpm | 200 rpm | 100 rpm | 6 rpm | 3 rpm |
| Maleated TOFA amido amine (AN = 192 mg/g) | 10.7 | 298.2 | 183.8 | 142.1 | 96.8 | 45.0 | 42.7 |
| 9139-70-11 (LTFAM* AN = 163 mg/g) | 10.7 | 162.6 | 95.1 | 70.4 | 43.5 | 12.6 | 11.2 |
| 9160-57-11 (LTFAM* AN = 167.2 mg/g) | 10.7 | 147.9 | 83.6 | 60.7 | 36.5 | 10.3 | 9.3 |
| 9177-32-11 (LTFAM* AN = 157.8 mg/g) | 10.7 | 156.7 | 88.7 | 64.3 | 38.2 | 9.4 | 8.2 |
| 9177-34-11 (LTFAM* AN = 147.9 mg/g) | 10.7 | 155.7 | 86.4 | 61.8 | 35.9 | 8.2 | 7.0 |
| 8998-75B-7 (LTFAM* AN = 188.35 mg/g) | 10.7 | 190 | 111 | 86.1 | 55.7 | 20.8 | 19.9 |
| 8998-75C-7 (LTFAM* AN = 181.39 mg/g) | 10.7 | 193.1 | 111.1 | 82.1 | 51.2 | 15.4 | 13.8 |
| Maleated TOFA amido-amine - 2 (AN = 192 mg/g) | 10.7 | 368.9** | 237.3 | 187.6 | 133.6 | 66.1 | 64.7 |

*LTFAM—low titer fatty acid material.
**Estimated via the HB model.

While preferred embodiments of the present disclosure have been shown and described herein, it will be understood that such embodiments are provided by way of example only. Numerous variations, changes and substitutions will occur to those skilled in the art without departing from the spirit of the present disclosure. Accordingly, it is intended that the appended claims cover all such variations as fall within the spirit and scope of the invention. Furthermore, the system may comprise at least one device for charging and/or discharging the system or a plurality of devices for charging and/or discharging the system.

The contents of all references, patents, pending patent applications and published patents, cited throughout this application are hereby expressly incorporated by reference.

Those skilled in the art will recognize, or be able to ascertain using no more than routine experimentation, many equivalents to the specific embodiments of the present disclosure described herein. Such equivalents are intended to be encompassed by the following claims. It is understood that the detailed examples and embodiments described herein are given by way of example for illustrative purposes only, and are in no way considered to be limiting to the invention. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the present disclosure. Such equivalents are intended to be encompassed by the following claims.

What is claimed is:

1. A low gravity solid (LGS) tolerant emulsifier comprising a maleated amido-amine reaction product produced by:
    reacting (i) a fatty acid material and (ii) an amine material to produce an amido-amine reaction product; and
    reacting the amido-amine reaction product with maleic anhydride to produce the maleated-amido-amine reaction product, wherein the fatty acid material includes at least one of:

an acid number ranging from about 143 to about 200 mg/g;
a fatty acid concentration of about 34% to about 89%;
a rosin acid concentration of about 11% to about 50%;
a titer point of less than about 14° C.;
a PAN rosin acid concentration of less than or equal to about 50%;
heavies present in an amount of less than or equal to about 40% of the fatty acid material, wherein the heavies are fatty acids or rosin acids that have a boiling point higher than monomer fatty and rosin acids formed during a distillation process;
a Gardner color index in a range from about 4.0 to about 17.0, wherein the Gardner color index is determined with ASTM D6166-12 (2016);
one or more of: C18 type fatty acids is present in an amount of about 25 to about 89%, C20 type fatty acids is present in an amount of less than or equal to about 34%, and C16 type fatty acids is present in an amount of no greater than about 5%; or
a combination thereof.

2. The emulsifier of claim 1, wherein at least one of:
the fatty acid material is present in an amount of about 55 wt. % to about 95 wt. % of the amido-amine reaction product;
the amine material is present in an amount of about 5 wt. % to about 45 wt. % of the amido-amine reaction product;
the maleic anhydride is present in an amount of about 1 wt. % to about 20 wt. % of the maleated amido-amine reaction product or the emulsifier; or
a combination thereof.

3. The emulsifier of claim 1, wherein the fatty acid material has an acid number ranging from about 155 to about 174 mg/g.

4. The emulsifier of claim 1, wherein the fatty acid material includes at least one of:
a side stream from the oil collected as the bottoms product during the production of low rosin (<5%) and low Gardner Color index (<7.0) tall oil fatty acid (TOFA) from refinery columns during the distillation of crude tall oil (CTO);
a mixture of the side stream and at least one of distilled tall oil, TOFA, rosin, or a combination thereof;
a product stream of the CTO refining process;
a mixture of TOFA and distilled tall oil;
a mixture of distilled tall oil and rosin;
a mixture of TOFA and rosin;
a disproportionated tall oil, a mixture of disproportionated tall oil and rosin, a mixture of disproportionated tall oil and TOFA, a mixture of disproportionated tall oil and distilled tall oil, or a combination thereof; or
a combination thereof.

5. The emulsifier of claim 1, wherein the amine material has an amine value of about 700 to about 1300 mg/g.

6. The emulsifier of claim 1, wherein the amine material has an amine value of about 700 to about 900 mg/g.

7. The emulsifier of claim 1, wherein the amine material is or includes a distillation residuum bottom composition of a reaction product of monoethanolamine and ammonia in which piperazine distillate product has been recovered.

8. The emulsifier of claim 1, wherein the amine material includes at least one of: diethylenetriamine (DETA), hydroxyethyldiethylenetriamine (HEDETA), 2-piperazinoethanol, triethylenetetramine (TETA), Tetraethylenepentamine (TEPA), pentaethylene hexamine (PEHA) heptaethyleneoctamine (HEOA), hexaethyleneheptamine (HEHA) amine HST, amine DCT, aminoethylpiperazine (AEP), dimethylaminopropylamine (DMAPA), aminoethylethanolamine (AEEA), diethanolamine (DEA), triethanolamine (TEA), monoethanolamine, or combinations thereof.

9. The emulsifier of claim 1, wherein the amido-amine reaction product includes at least one of bis-amidoamines, alkanolamides, di-ester alcohol amine, ester alcohol amine, di-ester amine, ester amido amines, amido amine alcohols, amides of the hydroxy piperazine, amide imidazoline, ester imidazoline, amine imidazoline, alkanol imidazoline or combinations thereof.

10. An invert emulsion fluid (IEF) comprising the emulsifier of claim 1, and at least one of: a non-aqueous continuous phase, a discontinuous hygroscopic phase like brine, an additive, or a combination thereof.

11. The IEF of claim 10, further comprising greater than about 10% V/V of low gravity solids having a specific gravity of about 2.0 to about 3.0.

12. The IEF of claim 10, further comprising about 4 to about 12% V/V of low gravity solids having a specific gravity of about 2.0 to about 3.0.

13. The IEF of claim 10, wherein the IEF has a high temperature, high pressure fluid loss of about 1 to about 20 mL at 350° F.

14. The IEF of claim 10, wherein the IEF has a lower rheology than an IEF comprising a maleated tall oil fatty acid (TOFA) amine emulsifier.

15. The IEF of claim 10, wherein the IEF has at least one of:
a rheology that is about 10-about 92% lower that a similarly formulated IEF comprising a maleated tall oil fatty acid (TOFA) amine emulsifier as determined by taking readings from 600 rpm to 3 rpm at 150° F.;
a gel strength that is about 10 to about 92% lower than a similarly formulated IEF with a maleated TOFA amine emulsifier at 150° F.;
a yield stress (Tau0) that is less than a similarly formulated IEF with a maleated TOFA when measured at 150° F.; or
a combination thereof.

16. The IEF of claim 10, wherein the IEF is used for gas drilling and/or oil drilling.

17. The IEF of claim 10, wherein the additive includes at least one of: a rheology modifier, emulsifier, wetting agent, viscosifier, lime, salt, fluid loss additive, lost circulation material, weighting agent, or a combination thereof.

18. A drilling fluid comprising the IEF of claim 10.

19. A method of drilling a well, the method comprising drilling a well bore and circulating the drilling fluid of claim 18 through said well bore when drilling the well bore.

20. The invert emulsion fluid (IEF) of claim 10, wherein the discontinuous hygroscopic phase is brine.

21. A method of making an emulsifier, the method comprising:
reacting (i) a fatty acid material comprising and (ii) an amine material to produce an amido-amine reaction product; and
reacting the amido-amine reaction product with maleic anhydride to produce a maleated amido-amine reaction product, wherein the fatty acid material includes at least one of:
an acid number ranging from about 143 to about 200 mg/g;
a fatty acid concentration of about 34% to about 89%;
a rosin acid concentration of about 11% to about 50%;
a titer point of less than about 14° C.;

a PAN rosin acid concentration of less than or equal to about 50%;

heavies present in an amount of less than or equal to about 40% of the fatty acid material, wherein the heavies are fatty acids or rosin acids that have a boiling point higher than monomer fatty and rosin acids formed during a distillation process;

a Gardner color index in a range from about 4.0 to about 17.0, wherein the Gardner color index is determined with ASTM D6166-12 (2016); or a combination thereof.

* * * * *